(12) United States Patent
Miyata

(10) Patent No.: US 6,919,326 B1
(45) Date of Patent: Jul. 19, 2005

(54) CARBONYL-STRESS IMPROVING AGENT AND PERITONEAL DIALYSATE

(75) Inventor: Toshio Miyata, 102 Ekuseru Isehara, 16-25, Sakuradai 2-chome, Isehara-shi Kanagawa 259-1132 (JP)

(73) Assignees: Toshio Miyata, Kanagawa (JP); Kiyoshi Kurakawa, Tokyo (JP); Tokai University Educational System, Tokyo (JP)

( * ) Notice: Subject to any disclaimer, the term of this patent is extended or adjusted under 35 U.S.C. 154(b) by 0 days.

(21) Appl. No.: 09/763,286

(22) PCT Filed: Aug. 23, 1999

(86) PCT No.: PCT/JP99/04521

§ 371 (c)(1),
(2), (4) Date: Aug. 28, 2001

(87) PCT Pub. No.: WO00/10606

PCT Pub. Date: Mar. 2, 2000

(30) Foreign Application Priority Data

Aug. 24, 1998 (JP) .......................... 10/237108
Jun. 2, 1999 (JP) .......................... 11/155393

(51) Int. Cl.$^7$ .................... A01N 43/00; A61K 31/33
(52) U.S. Cl. ............... 514/183; 514/2; 514/20; 514/23; 514/42; 514/832; 514/866
(58) Field of Search .................... 514/2, 20, 23, 514/42, 183, 832, 866

(56) References Cited

U.S. PATENT DOCUMENTS

| | | | |
|---|---|---|---|
| 3,284,531 A | 11/1966 | Shaw et al. | |
| 3,793,187 A | 2/1974 | Marx et al. | |
| 4,171,283 A | 10/1979 | Nakashima et al. | |
| 4,977,287 A | 12/1990 | Kakimoto et al. | |
| 5,128,360 A | * 7/1992 | Cerami et al. | 514/400 |
| 5,827,820 A | 10/1998 | duMoulin | |
| 5,855,882 A | 1/1999 | Li et al. | |
| 5,861,238 A | 1/1999 | Li et al. | |
| 5,868,936 A | 2/1999 | Ofsthun et al. | |
| 5,891,341 A | 4/1999 | Li et al. | 210/646 |
| 5,962,245 A | 10/1999 | Li et al. | |
| 6,727,285 B1 | 4/2004 | Haik, Jr. | |
| 2003/0143215 A1 | 7/2003 | Miyata | |

FOREIGN PATENT DOCUMENTS

| | | |
|---|---|---|
| EP | 0 242 855 A2 | 10/1987 |
| EP | 0 222 313 A2 | 5/1989 |
| EP | 2 316 852 A2 | 5/1989 |
| EP | 0 339 496 A2 | 11/1989 |
| EP | 0 359 112 A2 | 3/1990 |
| EP | 0 433 679 A2 | 6/1991 |
| EP | 0 474 874 A1 | 3/1992 |
| JP | 62-142114 A | 6/1987 |
| JP | 62-249908 A | 10/1987 |
| JP | 62-249909 A | 10/1987 |
| JP | 64-56615 A | 3/1989 |
| JP | 64-83059 | 3/1989 |
| JP | 2-156 A | 1/1990 |
| JP | 2-753 A | 1/1990 |
| JP | 2-765 A | 1/1990 |
| JP | 2-42053 A | 2/1990 |
| JP | 2-62885 A | 3/1990 |
| JP | 2-167264 A | 6/1990 |
| JP | 3-148220 A | 6/1991 |
| JP | 3-161441 A | 7/1991 |
| JP | 3-204874 | 9/1991 |
| JP | 3-240725 A | 10/1991 |
| JP | 3-261772 A | 11/1991 |
| JP | 4-9375 A | 1/1992 |
| JP | 4-502611 A | 5/1992 |
| JP | 4-187158 A | 7/1992 |
| JP | 4-308586 A | 10/1992 |
| JP | 5-9114 A | 1/1993 |
| JP | 5-105633 | 4/1993 | .......... A61K/31/70 |
| JP | 5-201993 A | 8/1993 |
| JP | 5-505189 A | 8/1993 |
| JP | 5-255130 A | 10/1993 |
| JP | 5-310565 A | 11/1993 |
| JP | 6-9380 A | 1/1994 |
| JP | 6-135698 A | 5/1994 |
| JP | 6-192089 A | 7/1994 |
| JP | 6-206818 A | 7/1994 |
| JP | 6-256280 A | 9/1994 |
| JP | 6-507822 A | 9/1994 |
| JP | 6-287179 A | 10/1994 |

(Continued)

OTHER PUBLICATIONS

Tanaka, Yasushi et al., "Inhibitory Effect of Metformin on Formation of Advanced Glycation End Products" Current Therapeutic Research, Oct. 1997, 58 (10), 693–697.*
Lo et al., *J. Biol. Chem.* 269(51)32299–32306 (1994).
Niquette et al., *J. Am. Water Works Assoc.* 90(1):96–97 (1998).
Tanaka et al., *Current Therapeutic Research* 58(10)693-7 (1997).

(Continued)

*Primary Examiner*—James O. Wilson
*Assistant Examiner*—Patrick Lewis
(74) *Attorney, Agent, or Firm*—Karl Bozicevic; Bozicevic, Field & Francis LLP

(57) ABSTRACT

Carbonyl compounds generated and accumulated in the peritoneal dialysate can be inactivated or eliminated by a carbonyl compound-trapping agent such as aminoguanidine. Carbonyl compounds generated during sterilization and storage of the peritoneal dialysate can be eliminated by pre-contacting with the trapping agent. Further, it is possible to eliminate carbonyl compounds transferred from the blood to the peritoneal cavity of the patient during peritoneal dialysis treatment, by adding the trapping agent to the peritoneal dialysate or by circulating the fluid through a carbonyl compound-trapping cartridge. Intraperitoneal protein modification by carbonyl compounds is inhibited by the present invention, thereby sufficiently reducing peritoneal disorders associated with peritoneal dialysis treatment.

9 Claims, 27 Drawing Sheets

FOREIGN PATENT DOCUMENTS

| | | |
|---|---|---|
| JP | 6-287180 A | 10/1994 |
| JP | 6-298737 A | 10/1994 |
| JP | 6-305964 A | 11/1994 |
| JP | 6-305969 A | 11/1994 |
| JP | 7-500580 A | 1/1995 |
| JP | 7-500811 A | 1/1995 |
| JP | 7-503713 A | 4/1995 |
| JP | 7-133264 A | 5/1995 |
| JP | 7-196498 A | 8/1995 |
| JP | 7-206838 | 8/1995 |
| JP | 7-247296 A | 9/1995 |
| JP | 8-59485 A | 3/1996 |
| JP | 8-131542 A | 5/1996 |
| JP | 8-157473 A | 6/1996 |
| JP | 9-40519 A | 2/1997 |
| JP | 9-40626 A | 2/1997 |
| JP | 59258 A | 3/1997 |
| JP | 9-59233 A | 3/1997 |
| JP | 9-124471 A | 5/1997 |
| JP | 9-221427 A | 8/1997 |
| JP | 9-241165 A | 9/1997 |
| JP | 9-315960 A | 12/1997 |
| JP | 63-19149 A * | 1/1998 |
| JP | 10-158244 A | 6/1998 |
| JP | 10-158265 A | 6/1998 |
| JP | 10-167965 A | 6/1998 |
| JP | 10-175954 A | 6/1998 |
| JP | 10-182-460 A | 7/1998 |
| WO | WO 90/06102 | 6/1990 |
| WO | WO 91/11997 | 8/1991 |
| WO | WO 91/12800 | 9/1991 |
| WO | WO 92/11853 | 7/1992 |
| WO | WO 93/14750 | 8/1993 |
| WO | WO 93/19792 A1 * 10/1993 ............ A61M/1/28 |  |
| WO | WO 94/04520 | 3/1994 |
| WO | WO 96/02838 | 2/1996 |
| WO | WO 96/11196 | 4/1996 |
| WO | WO 93/04690 | 10/1996 |
| WO | WO 96/31537 | 10/1996 |
| WO | WO 97/09981 | 3/1997 |
| WO | WO 00/69466 | 11/2000 |
| WO | WO 01/24790 | 4/2001 |

OTHER PUBLICATIONS

Combet et al. (2000) "Vascular Proliferation and Enhanced Expression of Endothelial Nitric Oxide Synthase in Human Peritoneum Exposed to Long–Term Peritoneal Dialysis." *J. Am. Soc. Nephrol.*, vol. 11:717–728.

Combet et al. (1999) "Regulation of Aquaporin–1 and Nitric Oxide Synthase Isoforms in a Rat Model of Acute Peritonitis." *J. Am. Soc. Nephrol.*, vol. 10:2185–2196.

Faller (1996) "Amino acid–based peritoneal dialysis solutions." *Kidney International*, vol. 50(56):S–81–S–85.

Miyata et al. (2000) "Mechanism of the Inhibitory Effect of OPB–9195 [(±)–2–Isopropylidenehydrazono–4–oxo–thiazolidin–5– yl acetanilide] on Advanced Glycation End Product and Advanced Lipoxidation End Product Formation." *J>Am. Soc. Nephrol.*, vol. 11:1719–1725.

Miyata et al. (1996) "Accumulation of Albumin–Linked and Free–Form Pentosidine in the Circulation of Uremic Patients with End–Stage Renal Failure: Renal Implications in the Pathophysiology of Pentosidine." *Journal of the American Society of Nephrology*, vol. 7(8):1198–1206.

Miyata et al. (1998) "Accumulation of Carbonyls Accelerates the Formation of Pentosidine, an Advanced Glycation End Product: Carbonyl Stress in Uremia." *J. Am. Soc. Nephrol.*, vol. 9:2349–2356.

Miyata et al. (1998) "Autoxidation products of both carbohydrates and lipids are increased in uremic plasma: Is there oxidative stress in uremia?" *Kidney International*, vol. 54:1290–1295.

Miyata et al. (1999) "Alterations in nonenzymatic biochemistry in uremia: Origin and significance of "carbonyl stress" in long–term uremic complications." *Kidney International*, vol. 55:389–399.

Miyata et al. (1997) "Implication of an increased oxidative stress in the formation of advanced glycation end products in patients with end–stage renal failure." *Kidney International*, vol. 51:1170–1181.

Nakayama et al. (1997) "Immunohistochemical detection of advanced glycosylation end–products in the peritoneum and its possible pathophysiological role in CAPD." *Kidney International*, vol. 51:182–186.

Wilkie et al. (1997) "Polyglucose Solutions in CAPD." *Peritoneal Dialysis International*, vol. 17(2):S47–S50.

Yamada et al. (1994) "Immunohistochemical study of human advanced glycosylation end–products (AGE) in chronic renal failure." *Clinical Nephrology*, vol. 42(6):354–361.

Niwa et al., "Modification of Beta$_2$m with advanced glycation end products as observed in dialysis–related amyloidosis by 3–DG accumulating in uremic serum," *Kidney International* 49:861–867 (1996).

Miyata et al., "2–Isoproylidenehydrazono–4–oxo–thiazolid in–5– ylacetanilde (OPB–9195) treatment inhibits the development of intimal thickening after balloon injury of rat carotid artery; role of glycoxidation and lipoxidation reactions in vascular tissue damage." *FEBS Letters* 445(1):202–6 (1999).

Fishbane, et al., "Reduction of plasma apolipoprotein–B by effective removal of circulating glycation derivatives in uremia." *Kidney International* 52(6):1645–50 (1997).

Feather et al., "The Use of Aminoguanidine to Trap and Measure Dicarbonyl Intermediates Produced During the Maillard Reaction." *ACM Symp Ser 631* 631:24–31 (1996).

Booth et al., "In Vitro Kinetic Studies of Formation of Antigenic Advanced Glycation End Products (AGEs)." *The Journal of Biological Chemistry* 272(9):5430–7 (1997).

Ungar et al., "Inhibition of Binding of Aldehydes of Biogenic Amines in Tissues" *Biochem Pharmacol* 22(15):1905–13 (1973).

Jarret et al., "Elimiation du glyoxal et de l'acide glyoxylique par filtration sur charbon actif en grains" *Sci Eau* 5(4):377–400 (1986).

Chaudhuri et al., "Removal of carbonyl sulfide from a liquid hydrocarbon with activated alumina" *Sep Technol* 2(2):58–61 (1992).

Foote et al., "The Pharmacokinetics of Aminoguanidine in End–Stage Renal Disease Patients on Hemodialysis." *American Journal of Kidney Disease* 25(3):420–425 (Mar. 1995).

Nakamura et al., "Progression of Nephropathy in Spontaneous Diabetic Rats Is Prevented by OPB–9195, a Novel Inhibitor of Advanced Glycation" *Diabetes* 46(5):895–9 (1997).

Rahbar, "An abnormal hemoglobin in red cells of diabetics" *Clinica Chimica Acta* 22:296–298 (1968).

Mailard, "Reaction Generale Des Acides Amines Sur Les Sucres: Ses Consequences Biologiques" *Compt Rend Soc Biol.* 72:599–603 (1912).

* cited by examiner

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 1
actggaccct ggctttactg c                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence
```

```
-continued

<400> SEQUENCE: 2
ttggtgaggt ttgatccgca tg                                              22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3
cctgcaccac caactgctta gccc                                            24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4
gatgtcatca tatttggcag gtt                                             23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
ggcagaatca tcacgaagtg gtg                                             23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
ctgtaggaag ctcatctctc c                                               21
```

CARBONYL-STRESS IMPROVING AGENT AND PERITONEAL DIALYSATE

CROSS REFERENCES

This application is the national phase application of PCT application PCT/JP99/04521 filed Aug. 23, 1999 designating the United States which application claims priority to Japanese patent applications 10/237108 filed Aug. 24, 1998 and 11/155393 filed Jun. 2, 1999 to which applications is claimed priority.

TECHNICAL FIELD

The present invention relates to a peritoneal dialysate used for treating patients with renal failure.

BACKGROUND ART

Two types of dialysis, hemodialysis and peritoneal dialysis, are used to treat patients with chronic renal failure. Peritoneal dialysis is a method in which the dialysate is allowed to dwell in the peritoneal cavity for a certain period of time, thereby facilitating the excretion of waste products out of the body into the dialysate through the peritoneum. The dialysate is then recovered. Peritoneal dialysis is subdivided into intermittent peritoneal dialysis (IPD) and continuous ambulatory peritoneal dialysis (CAPD). CAPD is a method that incorporates the merits of the IPD method in which the fluid exchange is carried out about four times a day by lengthening the dwelling time of the perfusate in the peritoneal cavity.

Peritoneal dialysis has advantages such as being convenient and less time-consuming. However, it is known that long-term treatment with peritoneal dialysis can progressively lower the ability of water removal, and can result in abdominal protein denaturation and hardening, peritoneal fusion, and such abnormalities.

A part of the cause is thought to be glucose present in the peritoneal dialysate. Many types of peritoneal dialysates used today contain glucose as an osmoregulatory agent. Glucose is unstable to heat, and a part thereof is degraded during heat sterilization. As a result, highly reactive carbonyl compounds capable of modifying proteins may generate as degradation products. Such degradation products may also generate and accumulate in a glucose-containing peritoneal dialysate even during storage that follows sterilization.

Generally, glucose is apt to degrade at a nearly neutral or alkaline pH, and therefore, acidic buffers (pH 5.0–5.4) are selected to maintain the stability of glucose in ordinary peritoneal dialysates. However, such acidic buffers carry risks such as suppressing immunological defense mechanisms of peritoneal macrophages, causing the onset of peritonitis due to bacterial infection, and being cytotoxic to peritoneal mesothelial cells. To overcome such mutually contradictory problems, there was a desperate need to prevent generation of carbonyl compounds resulting from the degradation of glucose within peritoneal dialysates around a neutral pH, or eliminate such compounds.

On the other hand, a peritoneal dialysate formulated with a high concentration of glucose can modify proteins, and therefore, such dialysates are unfavorable for the peritoneum. From such a viewpoint, some peritoneal dialysates have been developed by utilizing glucose polymers that generate few degradation products (Unexamined Published Japanese Patent Application (JP-A) NO. Hei 10-94598; Wilkie, M. E. et al., Perit. Dial. Int., 17: S47–50 (1997)).

From the same viewpoint, other compounds have been proposed in place of glucose as osmoregulatory agents used in peritoneal dialysates. These include, cyclodextrin (JP-A Hei 8-71146), disaccharide (JP-A Hei 8-131541), and amino acids (Faller, B. et al., Kidney Int., 50 (suppl.56), S81–85 (1996)). A peritoneal dialysate having cysteine as an additive to prevent the degradation of glucose has also been disclosed (JP-A Hei 5-105633).

These methods aim to improve inconveniences caused by the high concentration of glucose within the peritoneal dialysate.

It has been reported that, irrespective of the presence or absence of hyperglycemia, large amounts of highly reactive carbonyl compounds and AGE (advanced glycation end products) are accumulated in the blood and tissues of patients with chronic renal failure (Miyata, T. et al., Kidney Int., 51:1170–1181 (1997); Miyata, T. et al., J. Am. Soc. Nephrol., 7: 1198–1206 (1996); Miyata, T. et al., Kidney int. 54:1290–1295 (1998); Miyata, T. et al., J. Am. Soc. Nephrol.9:2349–2356 (1998)). Renal failure often accompanies conditions having an overload of carbonyl compounds (carbonyl stress). This carbonyl stress results from non-enzymatic biochemical reactions to generate carbonyl compounds from sugars and lipids, which is thought to lead to enhanced protein modifications (Miyata, T. et al., Kidney Int. 55:389–399 (1999)). Carbonyl stress not only alters the architecture of matrix proteins such as collagen and fibronectin, but also participates in the enhancement of peritoneal permeability and the onset of inflammation due to the physiological activities of carbonyl compounds towards a variety of cells.

In peritoneal dialysis, waste products in the blood are excreted into the peritoneal dialysate through the peritoneum. A hyperosmotic peritoneal dialysate dwelling within the peritoneal cavity collects highly reactive carbonyl compounds accumulated in the blood of renal failure patients through the peritoneum into itself. Thus, the carbonyl-compound concentration in the peritoneal dialysate elevates, resulting in a carbonyl-stress state. This is thought to cause carbonyl modification of proteins in the peritoneal cavity and as a consequence, the peritoneal functions are suppressed to advance peritoneal sclerosis.

Immunohistochemical examination of the endothelium and mesothelium, has demonstrated that the carbonyl-stress state is caused by glucose present in the peritoneal cavity in peritoneal-dialysis patients (Yamada, K. et al., Clin. Nephrol., 42: 354–361 (1994); Nakayama, M. et al.; Kidney Int., 51: 182–186 (1997); Miyata, T. et al., J. Am. Soc. Nephrol. in press; Combet, S. et al., J. Am. Soc. Nephrol. in press; Inagi, R. et al., J. Am. Soc. Nephrol. in press).

DISCLOSURE OF THE INVENTION

An objective of the present invention is to provide a method for reducing damage from carbonyl compounds during peritoneal dialysis, specifically for improving the carbonyl-stress state, as well as to provide a dialysate and pharmaceutical agent required for this method. The "carbonyl compound" in the present invention means a carbonyl compound derived from patients undergoing peritoneal-dialysis, a carbonyl compound generated in the peritoneal dialysate during manufacturing or storing, and a carbonyl compound generated in the peritoneal cavity during peritoneal dialysis. The present invention aims to minimize as much as possible the damages from these carbonyl compounds on the patients undergoing dialysis.

The present inventors have discovered that the highly reactive carbonyl compounds present in the peritoneal dialysate in peritoneal dialysis patients are not merely those present in the original peritoneal dialysate that have been infused into the peritoneal cavity. Specifically, the amount of glucose-excluded carbonyl compounds in the peritoneal dialysate recovered from peritoneal-dialysis patients is five times more than the amount before dialysis, and thus, the majority of the carbonyl compounds is assumed to derive from blood (FIG. 1). Therefore, it has been revealed that the carbonyl compounds present in the peritoneal dialysate in the peritoneal cavity, include not only carbonyl compounds generated in the process of heat sterilization and those that accumulate during storage, but also those that are derived from blood and those that generate and accumulate within the peritoneal cavity during dialysis, the latter two being not negligible. Immunohistochemical examinations of peritoneal tissue from peritoneal-dialysis patients have revealed the presence of carbonyl-modified proteins (FIG. 2). Accordingly, if it is possible to remove carbonyl compounds transferred from the blood into the peritoneal cavity during peritoneal dialysis, the carbonyl-stress state would also be effectively improved.

The present inventors thought that renal failure should often accompany conditions in which in vivo protein modification was enhanced and that, when glucose was continuously infused at a high concentration into the peritoneal cavity by a method such as peritoneal dialysis, intraperitoneal proteins would be increasingly susceptible to non-enzymatic modifications due to the peritoneal dialysate in which peritoneal cavity-derived carbonyl compounds were accumulated (FIG. 7).

Based on such a background, the present inventors have discovered that a carbonyl compound-trapping agent is effective in preparing a dialysate capable of reducing carbonyl compounds of peritoneal dialysate origin, and thus, completed the present invention. Focusing mainly on carbonyl compounds that accumulate within blood, the present inventors have further found that pharmaceutical agents that prevent protein modifications caused by carbonyl stress and such peritoneal dialysis-associated complications, are useful, thereby further completing the present invention.

Specifically, the present invention relates to a carbonyl-stress improving agent, and a peritoneal dialysate based thereon, as well as a pharmaceutical agent. The present invention relates more specifically to:

(1) an agent for improving intraperitoneal carbonyl-stress state during peritoneal dialysis, comprising a carbonyl compound-trapping agent as an active ingredient;
(2) the agent of (1), wherein the carbonyl compound-trapping agent is immobilized on an insoluble carrier;
(3) the agent of (1), wherein the carbonyl compound-trapping agent is to be mixed with a peritoneal dialysate;
(4) the agent of any one of (1) to (3), wherein the carbonyl compound-trapping agent is selected from the group consisting of aminoguanidine, pyridoxamine, hydrazine, SH group containing compound, and derivatives of these;
(5) the agent of any one of (1) to (3), wherein the carbonyl compound-trapping agent is an agent inhibiting Maillard reaction;
(6) the agent of (1), wherein the carbonyl compound-trapping agent is a compound insoluble in peritoneal dialysates and capable of adsorbing carbonyl compounds;
(7) a cartridge used for trapping carbonyl compounds within peritoneal dialysates, wherein the cartridge is filled with the carbonyl compound-trapping agent(s) of (2) and/or (6);
(8) a method for preparing a peritoneal dialysate having a reduced carbonyl compound content, the method comprising passing the peritoneal dialysate through the cartridge of (7);
(9) a method for preparing a peritoneal dialysate having a reduced carbonyl compound content, the method comprising:
(a) contacting the peritoneal dialysate with the carbonyl compound-trapping agent(s) of (2) and/or (6) and
(b) separating the peritoneal dialysate from the carbonyl compound-trapping agent;
(10) a peritoneal dialysate comprising a carbonyl compound-trapping agent;
(11) the peritoneal dialysate of (10), wherein the peritoneal dialysate further comprises a reducing sugar, and is placed in a container comprising a first compartment and a second compartment so that the first compartment contains the reducing sugar and the second compartment contains the carbonyl compound-trapping agent; and
(12) the peritoneal dialysate of (10), wherein the carbonyl compound-trapping agent is to be administered into the intraperitoneal cavity.

The present invention further relates to the use of carbonyl compound-trapping agent for improving intraperitoneal carbonyl-stress state. The present invention also relates to the use of carbonyl compound-trapping agent for the peritoneal dialysis treatment. Furthermore, the present invention relates to the use of carbonyl compound-trapping agent for producing an agent improving carbonyl stress.

In the present invention, the carbonyl compounds to be trapped include, for example, carbonyl compounds generated in the processes of production and storage of a peritoneal dialysate. As described above, carbonyl compounds can always be generated in a peritoneal dialysate containing a high concentration of glucose as an osmoregulatory agent. Such carbonyl compounds include, for example, the following compounds (Richard, J. U. et al., Fund. Appl. Toxic., 4: 843–853 (1984)):

3-deoxyglucosone
5-hydroxymethylfurfural (abbreviated hereafter "5-HMF")
formaldehyde
acetaldehyde
glyoxal
methylglyoxal
levulinic acid
furfural
arabinose In the present invention, a carbonyl compound-trapping agent is used throughout the dialysis, thereby achieving the removal of carbonyl compounds, as listed below, which are accumulated in the blood of a patient with renal failure and are transferred into the peritoneal cavity following peritoneal dialysis, as well as the removal of carbonyl compounds generated in a peritoneal dialysate during its production process and storage process.

Carbonyl compounds derived from ascorbic acid:
dehydroascorbic acid

Carbonyl compounds derived from carbohydrate, lipid, or amino acid:

glyoxal methylglyoxal 3-deoxyglucosone hydroxynonenal malondialdehyde acrolein

A preferred carbonyl compound-trapping agent in the present invention is one capable of completely inhibiting or reducing the protein-modification activity of all these carbonyl compounds through a chemical reaction or adsorption; however the carbonyl compound-trapping agent also includes an agent effective merely for major carbonyl compounds among these. For example, methylglyoxal is believed to have a relatively high reactivity among carbonyl compounds (see Thornalley, R. J., Endocrinol. Metab. 3 (1996) 149–166; Inagi, R. et al., J. Am. Soc. Nephrol. in press; and Example 3), and therefore it is of great pathophysiological significance to inhibit the activity of methylglyoxal. Consequently, a compound effective for methylglyoxal can be a preferred carbonyl compound-trapping agent of the present invention. Specifically, as indicated in Examples, compounds such as activated charcoal, guanidine, aminoguanidine, biguanide, cysteine, and albumin are particularly effective carbonyl compound-trapping agents for methylglyoxal.

Although some carbohydrates used as osmoregulatory agents have been reported to be more stable than glucose, it is difficult to completely inhibit the generation of carbonyl compounds from these carbohydrates during heat sterilization and storage processes. Thus, the use of the carbonyl compound-trapping agent is meaningful in situations where carbohydrates other than glucose are used as osmoregulatory agents. Carbohydrates other than glucose usable as osmoregulatory agents in peritoneal dialysis, include, trehalose (JP-A Hei 7-323084), hydrolyzed starch (JP-A Hei 8-85701), maltitol and lactitol (JP-A Hei 8-131541), as well as non-reducing oligosaccharides and non-reducing polysaccharides (JP-A Hei 10-94598).

Carbonyl compound-trapping agents of the present invention include compounds capable of inhibiting or reducing the damage due to carbonyl compounds towards dialysis patients by a chemical reaction or adsorption, and which per se is safe for the patients. Such compounds include those listed below. The inventive carbonyl compound-trapping agent can be used alone or in combination of two or more types of compounds.

aminoguanidine (Foote, E. F. et al., Am. J. Kidney Dis., 25: 420–425 (1995))

±2-isopropylidenehydrazono-4-oxo-thiazolidin-5-yl-acetanilide (OPB-9195; S. Nakamura, 1997, Diabetes 46:895–899)

Further, the carbonyl compound-trapping agent includes, for example, the following compounds or derivatives thereof that are capable of functioning as a carbonyl compound-trapping agent. The "derivatives" indicate compounds having an atomic or molecular substitution(s) at any position as compared with the parental compound.

(1) guanidine derivatives such as methylguanidine (JP-A Sho 62-142114; JP-A Sho 62-249908; JP-A Hei 1-56614; JP-A Hei1-83059; JP-A Hei 2-156; JP-A Hei 2-765; JP-A Hei 2-42053; JP-A Hei 6-9380; Published Japanese Translation of International Publication 5-505189), etc.

(2) hydrazine derivatives such as sulfonylhydrazine, etc.

(3) 5-membered heterocyclic compounds having 2 nitrogen atoms, such as pyrazolone (JP-A Hei 6-287179), pyrazoline (JP-A Hei10-167965), pyrazole (JP-A Hei 6-192089; JP-A Hei6-298737; JP-A Hei 6-298738), imidazolysine (JP-A Hei 5-201993; JP-A Hei 6-135968; JP-A Hei7-133264; JP-A Hei10-182460), hydantoin (JP-A Hei6-135968), etc.

(4) 5-membered heterocyclic compounds having 3 nitrogen atoms, such as triazole (JP-A Hei 6-192089), etc.

(5) 5-membered heterocyclic compounds having a nitrogen atom and a sulfur atom, such as thiazoline (JP-A Hei 10-167965), thiazole (JP-A Hei 4-9375; JP-A Hei 9-59258), thiazoline (JP-A Hei 5-201993; JP-A Hei 3-261772; JP-A Hei 7-133264; JP-A Hei 8-157473), etc.

(6) 5-membered heterocyclic compounds having a nitrogen atom and an oxygen atom, such as oxazole (JP-A Hei 9-59258), etc.

(7) nitrogen-containing 6-membered heterocyclic compounds such as pyridine (JP-A Hei 10-158244; JP-A Hei 10-175954), pyrimidine (Published Japanese Translation of International Publication 7-500811), etc.

(8) nitrogen-containing condensed heterocyclic compounds such as indazole (JP-A Hei 6-287180), benzimidazole (JP-A Hei 6-305964), quinoline (JP-A Hei 3-161441), etc.

(9) sulfur- and nitrogen-containing condensed heterocyclic compounds such as benzothiazole (JP-A Hei 6-305964), etc.

(10) sulfur-containing condensed heterocyclic compound such as benzothiophene (JP-A Hei 7-196498), etc.

(11) oxygen-containing condensed heterocyclic compounds such as benzopyran (JP-A Hei 3-204874; JP-A Hei 4-308586), etc.

(12) nitrogenous compounds such as carbazoyl (JP-A Hei 2-156; JP-A Hei 2-753), carbazic acid (JP-A Hei 2-167264), hydrazine (JP-A Hei 3-148220), etc.

(13) quinones such as benzoquinone (JP-A Hei 9-315960), hydroquinone (JP-A Hei 5-9114), etc.

(14) aliphatic dicarboxylic acids (JP-A Hei 1-56614; JP-A Hei 5-310565)

(15) suicides (JP-A Sho 62-249709)

(16) organogermanes (JP-A Hei 2-62885; JP-A Hei 5-255130; JP-A Hei 7-247296; JP-A Hei 8-59485)

(17) flavonoids (JP-A Hei 3-240725; JP-A Hei 7-206838; JP-A Hei 9-241165; WO 94/04520)

(18) alkylamines (JP-A Hei 6-206818; JP-A Hei 9-59233; JP-A Hei 9-40626; JP-A Hei 9-124471)

(19) amino acids (Published Japanese Translation of International Publication 4-502611; Published Japanese Translation of International Publication 7-503713)

(20) aromatic compounds such as ascochlorin (JP-A Hei 6-305959), benzoic acid (WO 91/11997), pyrrolonaphthyridinium (JP-A Hei 10-158265), etc.

(21) polypeptides (Published Japanese Translation of International Publication 7-500580)

(22) vitamins such as pyridoxamine (WO 97/09981), etc.

(23) SH group-containing compounds such as glutathione, cysteine, N-acetylcysteine, etc.

(24) SH group-containing proteins such as reduced albumin, etc.

(25) tetracyclines (JP-A Hei 6-256280)

(26) chitosans (JP-A Hei 9-221427)

(27) tannins (JP-A Hei 9-40519)

(28) quaternary ammonium ion-containing compounds

(29) biguanide agents such as phenformin, buformin, metformin, etc.

(30) ion exchange resins

(31) inorganic compounds such as activated charcoal, silica gel, alumina, calcium carbonate, etc.

The above compounds include those collectively known as Maillard reaction inhibitors. The Maillard reaction is a non-enzymatic glycation reaction between a reducing sugar such as glucose, and an amino acid or protein. Focusing on a phenomenon of brown coloration in a mixture consisting of amino acid and reducing sugar upon heating, Maillard reported this reaction in 1912 (Maillard, L. C., Compt. Rend. Soc. Biol., 72: 599 (1912)). This Maillard reaction is involved in brown coloration of food during heating or storage, generation of aromatic components and taste, and protein denaturation. Therefore, this reaction has been mainly studied in the field of food chemistry.

In 1968, glycated hemoglobin (HbA1c), a micro fraction of hemoglobin, was identified in vivo, which was revealed to increase in patients with diabetes (Rahbar. S., Clin. Chim. Acta, 22:296 (1968)). These findings helped launch a wave of interest in the significance of in vivo Maillard reaction and the participation of the reaction in the onset of adult diseases such as diabetic complications and arteriosclerosis as well as the progress of aging. Agents inhibiting the in vivo Maillard reaction were explored intensively, resulting in the discovery of the above-mentioned compounds as agents inhibiting the Maillard reaction.

However, it was not known that such Maillard reaction inhibitors are capable of improving carbonyl-stress state in peritoneal-dialysis patients and inhibit peritoneal dialysis-associated complications caused by carbonyl stress, by eliminating carbonyl compounds derived from the peritoneal dialysate and from the blood.

The inventive carbonyl compound-trapping agents include macro-molecular compounds such as ion exchange resins, or inorganic compounds such as activated charcoal, silica gel, alumina, and calcium carbonate, as well as organic compounds represented by the above-mentioned Maillard reaction inhibitors. These compounds are agents trapping insoluble carbonyl compounds in the peritoneal dialysate by utilizing their carbonyl compound-adsorbing activity. These compounds, though known to be chromatographic carriers, were not known to be useful for improving the carbonyl-stress state.

Adsorptive blood purifiers using activated charcoal have been in use for purifying blood in cases of drug poisoning or hepatic coma. They were also used in auxiliary treatment associated with hemodialysis for the removal of various endotoxins, exotoxins, and vasoactive substances that increase at the early stage of acute renal failure in multiple organ failure. However, it has been unknown that adsorptive blood purifiers are useful for removing carbonyl compounds present in the peritoneal dialysates or carbonyl compounds accumulated in the peritoneal cavity during the dialysis.

JP-A Sho 58-169458 describes an invention relating to a peritoneal dialysate containing a solid particulate absorbent and a method of peritoneal dialysis using this peritoneal dialysate. According to the publication, the solid particulate absorbent is added for the purpose of eliminating creatinine and low-molecular-weight metabolites; however, there is no description of effectiveness of the absorbent for the elimination of the carbonyl compounds accumulated in the peritoneal dialysate or in the peritoneal cavity during dialysis.

Further, the publication does not indicate nor suggest that the carbonyl-stress state of peritoneal-dialysis patients can be improved by the method of peritoneal dialysis.

The composition of the peritoneal dialysate used as a base to which the inventive carbonyl compound-trapping agent is added, may be any conventional dialysate. A peritoneal dialysate generally comprises an osmoregulatory agent, a buffering agent, and an inorganic salt. The sugars as listed above are used as osmoregulatory agents. In view of the stability of glucose, a buffer agent giving acidic pH (pH 5.0–5.4) is frequently used. Of course, when the osmoregulatory agent is not glucose, the buffering agent can be suitably selected to give a more physiological pH (pH of around 7.0). Alternatively, a product form has been designed, in which the buffering agent that adjusts pH at the time of use is packaged separately, allowing the use of both glucose and a neutral pH. In the present invention, carbonyl compounds generated in the processes of heat sterilization and long-term storage are eliminated, enabling the preferable use of a buffer system capable of giving neutral pH. Such a formulation has previously been difficult because of the degradation of glucose. A peritoneal dialysate generally contains inorganic salts such as sodium chloride, calcium chloride, or magnesium chloride. These salts bring peritoneal dialysates closer to physiological conditions, and are expected to give greater biocompatibility.

The inventive carbonyl compound-trapping agent can be added to a peritoneal dialysate of a known composition at the time of formulation, and the formulated and sealed dialysate can be sterilized by heating. It is expected that the addition of the agent sufficiently prevents the generation of carbonyl compounds from the major constituents during heat sterilization. Alternatively, the peritoneal dialysate is placed in a compartmentalized container comprising a first compartment and a second compartment; a reducing sugar is placed in the first compartment and the carbonyl compound-trapping agent is placed in the second compartment, and the two are mixed immediately before use. In this case, carbonyl compounds generated in the processes of sterilization and storage immediately bind to the carbonyl compound-trapping agent mixed. The excess carbonyl compound-trapping agents also trap blood-derived carbonyl compounds, after being administered into the peritoneal cavity. A single carbonyl compound-trapping agent or a combination of multiple trapping agents may be added to the peritoneal dialysate.

There can be many types of methods for contacting a peritoneal dialysate with a carrier on which a carbonyl compound-trapping agent is immobilized, or with carbonyl compound-trapping agents that are insoluble in the peritoneal dialysate. For example, the peritoneal dialysate is enclosed in a container where the carbonyl compound-trapping agent is immobilized inside, or in a container carrying a carbonyl compound-trapping agent immobilized on particulates or fibrous carriers, thereby trapping carbonyl compounds that generate and accumulate during storage. In the latter system, the insoluble carriers can be separated from the peritoneal dialysate by filtration. Alternatively, a carbonyl compound-trapping cartridge is prepared by filling a column with carrier beads or fibrous carriers on which the carbonyl compound-trapping agent is immobilized, or with a carbonyl compound-trapping agent which per se is insoluble in the peritoneal dialysate. Then, the peritoneal dialysate is contacted with the carrier in the cartridge, and then the fluid is infused into the peritoneal cavity. It is preferred that distilled water is pre-filled in the cartridge to prevent air bubbles at the start of peritoneal dialysis. When the carbonyl compound-trapping cartridge is contacted with the peritoneal dialysate at the time of peritoneal infusion, although it is impossible to remove patient-derived carbonyl compounds that accumulate in the fluid during the dialysis, carbonyl compounds originally present in the dialysate can be eliminated. Alternatively, when peritoneal dialysis treatment is conducted by using a closed circuit where the peritoneal dialysate is circulated by a small circulating pump, it is possible to attain the removal of not only carbonyl compounds originally present in the dialysate but also those that accumulate in the peritoneal cavity during dialysis, by installing within the circuit, the above-mentioned carbonyl compound-trapping cartridge containing carriers with immobilized carbonyl compound-trapping agent.

There is no particular restriction on the carrier that is used for immobilizing the inventive carbonyl compound-trapping agent, as long as the carrier is harmless to the human body and is sufficiently safe and stable as a material that is directly in contact with the peritoneal dialysate. The carriers include, for example, synthetic or naturally-occurring organic macromolecular compounds, and inorganic materials such as glass beads, silica gel, alumina, and activated charcoal, as well as these materials coated with a polysaccharide or synthetic polymer. Conventional modifications, reformations or denaturations can improve the permeability, drug compatibility, protective strength, adsorption capacity, or carbonyl compound specificity of the carries on which the carbonyl compound-trapping agent is immobilized, or the carbonyl compound-trapping agent, which per se is insoluble in the peritoneal dialysate.

A carrier comprising a macromolecule is exemplified by a polymethyl methacrylate polymer, polyacrylonitrile polymer, polysulfone polymer, vinyl polymer, polyolefin polymer, fluorine polymer, polyester polymer, polyamide polymer, polyimide polymer, polyurethane polymer, polyacryl polymer, polystyrene polymer, polyketone polymer, silicon polymer, cellulose polymer, chitosan polymer; specifically, polysaccharides such as agarose, cellulose, chitin, chitosan, sepharose, dextran, etc. and derivatives thereof, and polyester, polyvinyl chloride, polystyrene, polysufone, polyethersulfone, polypropylene, polyvinyl alcohol, polyarylether sulfone, polyacrylic ester, polymethacrylic ester, polycarbonate, acetylated cellulose, polyacrylonitrile, polyethylene terephthalate, polyamide, silicone resin, fluororesin, polyurethane, polyetherurethane, and polyacrylamide and derivatives thereof. The macromolecular material can be used alone or in a combination of two or more types of macromolecules. In the latter case, at least one of the macromolecules bears the carbonyl compound-trapping agent immobilized on it. The immobilized carbonyl compound-trapping agent is used alone or in a combination of two or more types of compounds. The above-mentioned polymer material may be a polymer comprising a single type of monomer or a copolymer comprising multiple types of monomers. Further, the material may be treated by the addition of an appropriate modifier, or may be subjected to denaturation treatment such as radiation cross-linking or cross-linking using peroxide.

There is no restriction on the shape of carrier. For example, the carrier can be membranous, fibrous, granular-shaped, hollow fiber-like, non-woven fabric-like, porous, or honeycomb-shaped. The carrier's area of contact with the peritoneal dialysate can be controlled by varying the thickness, surface area, diameter, length, shape, and/or size of the carrier. Further, the carbonyl compound-trapping agent can be immobilized on the inner wall of container, where the peritoneal dialysate is placed, and also within the circuit where the peritoneal dialysate is circulated.

The carbonyl compound-trapping agent can be immobilized on the above-mentioned carrier by using known methods, such as physical adsorption, specific biochemical binding reaction, ion binding, covalent bonding, grafting, etc. If necessary, a spacer can be inserted between the carrier and the carbonyl compound-trapping agent. When the carbonyl compound-trapping agent exhibits toxicity, the amount released becomes a vital issue. Thus, it is preferred that the carbonyl compound-trapping agent is immobilized on the carrier by covalent bonding so as to minimize the released amount. Functional groups in the carrier are utilized for covalently bonding the carbonyl compound-trapping agent thereto. The functional group is, for example, hydroxyl group, amino group, aldehyde group, carboxyl group, thiol group, silanol group, amide group, epoxy group, succinylimino group, etc.; however, the functional group is not limited to these groups. The covalent bond is, for example, ester linkage, ether linkage, amino linkage, amid linkage, sulfide linkage, imino linkage, disulfide linkage or the like.

A commercially available product, for example polystyrene carrier having sulfonylhydrazine groups (PS-TsNHNH2, ARGONAUT TECHNOLOGIES CO.), can be used as a carrier for immobilizing carbonyl compound-trapping agent.

The carrier with the immobilized carbonyl compound-trapping agent of the present invention can be sterilized by an appropriate sterilization method selected from publicly known sterilization methods depending upon the types of carbonyl compound-trapping agent and carrier used. The sterilization method includes, for example, high-pressure steam sterilization, gamma-ray irradiation sterilization, gas sterilization, etc. A cartridge, which is filled with the insoluble carbonyl compound-trapping agent or carrier with immobilized carbonyl compound-trapping agent, is connected with a container containing the peritoneal dialysate to simultaneously sterilize both the cartridge and container.

The carbonyl compound may be insufficiently eliminated from the peritoneal dialysate when only a small amount of carbonyl compound-trapping agent is in contact with the peritoneal dialysate. In general, it is hard to predict the quantity of carbonyl compound present in the peritoneal dialysis. Accordingly, the carbonyl compound-trapping agent is used as much as possible without compromising the safety in patients so as to maintain the maximal effect. The dose of carbonyl compound-trapping agent can be controlled by altering the amount of carbonyl compound-trapping agent immobilized on the carrier or by altering the amount of carrier on which the carbonyl compound-trapping agent is immobilized at the time of use.

The carbonyl compound-trapping agent can also be infused into the peritoneal dialysis circuit through an appropriate mixing connector installed in the circuit. In this case, the carbonyl compound generated during sterilization and storage processes is trapped within the circuit.

Further, the carbonyl compound-trapping agent can be directly administered into the peritoneal cavity and mixed with the peritoneal dialysate in the peritoneal cavity. In this case, carbonyl compounds derived from the peritoneal dialysate and from the blood are inactivated in the peritoneal cavity.

Furthermore, prior to the infusion of peritoneal dialysate to a patient, or while the fluid is dwelling in the peritoneal cavity, the carbonyl compound-trapping agent is administered to the peritoneal-dialysis patient by intravenous injection or the like, thereby successfully achieving the improvement of carbonyl-stress state in the peritoneal cavity.

Preferred embodiments of the inventive peritoneal dialysate are specifically described below.

The composition of the base dialysate is generally as follows.

Glucose 1–5%w/v
Sodium ion 100–150 meq
Potassium ion 0–0.05 meq
Magnesium ion 0–2 meq
Calcium ion 0–4 meq
Chloride ion 80–150 meq
Buffering agent 10–50 mM
(organic acids such as lactic acid, citric acid, malic acid, acetic acid, pyruvic acid, and succinic acid)

This is only a general formula, and a more suitable composition is selected depending on the symptoms of the patient.

The inventive carbonyl compound-trapping agent is added in an effective amount to the above-indicated basic formula. For example, when aminoguanidine is used, the concentration is 1 mM or higher, preferably 10 mM or higher, more preferably 10 mM or higher but not higher than 100 mM. If the amount of carbonyl compound-trapping agent added is small, they might be used up for the carbonyl compounds generated in the processes of production and storage. As a consequence, the trapping agent is unable to treat carbonyl compounds transferred to the dialysate from the blood and tissues of a patient during dialysis. Particularly, it is hard to predict the quantity of carbonyl compounds transferred from the blood and tissues to the dialysate. Accordingly, the carbonyl compound-trapping agent is used as much as possible without compromising the safety of a patient so as to maintain the maximal effect. It has been known that aminoguanidine exhibits only a low toxicity to animals. According to "Registry of Toxic Effect of Chemical Substances" (1978), the half-lethal dose of aminoguanidine, which is subcutaneously administered, is 1258 mg/kg in rat, or 963 mg/kg in mouse. This compound is water-soluble. OPB-9195 can also be added similarly, to a concentration of 1 mM or higher, preferably 10 mM or higher, more preferably 10 mM or higher, but not higher than 100 mM.

The inventive peritoneal dialysate as formulated above is filled in an appropriate closed container, and subjected to sterilization. An effective sterilization includes heat sterilization such as high-pressure steam sterilization, and hot water sterilization. In this case, it is important to use a container that releases no toxic substances at a high temperature, and has enough strength to bear transportation after sterilization. A specific example of such a container is a flexible plastic bag made of polyvinyl chloride, polypropylene, polyethylene, polyester, or ethylene-vinyl acetate copolymer. Further, to avoid the deterioration of the fluid resulting from the influence of the outside air, the container filled with the peritoneal dialysate may be packaged using a high gas barrier packaging material.

Filter sterilization can be selected in place of heat sterilization. For example, the fluid is sterilized by filtration using a precision filter device with a membrane of about 0.2-$\mu$m pore size. This method is free of the generation of carbonyl compounds that result during heating. The filter-sterilized peritoneal dialysate is filled into a container such as a flexible plastic bag and then sealed. Because the series of processes from sterilization to transportation does not differ from the preparation of current dialysates, the inventive peritoneal dialysate can also be manufactured by a procedure comprising similar steps.

When the sterilization is achieved by heat sterilization including high-pressure heat sterilization, as long as the carbonyl compound-trapping agent used is sufficiently stable to a treatment such as heating, the trapping agent may be added when the peritoneal dialysate is formulated, prior to the heat sterilization process. This procedure reduces the generation and accumulation of dialysate-derived carbonyl compounds during heating. Of course, the carbonyl compound-trapping agent also functions to reduce the generation and accumulation of carbonyl compounds during storage and peritoneal dialysis.

When the carbonyl compound-trapping agent used is unstable to heat sterilization, it can be sterilized by a method that does not require heating. Such sterilization methods include, for example, filter sterilization. Alternatively, the carbonyl compound-trapping agent may be added to a sterilized peritoneal dialysate. There is no particular limitation on the timing of addition. For example, the carbonyl compound-trapping agent is preferably added to the fluid after sterilization, because in this case, the trapping agent can suppress not only the generation of carbonyl compounds during peritoneal dialysis, but also the generation and accumulation of carbonyl compounds in the peritoneal dialysate during the storage prior to dialysis.

Alternatively, the carbonyl compound-trapping agent can be added immediately before peritoneal dialysis treatment or at the time of treatment. For example, the base solution and the carbonyl compound-trapping agent are placed separately in the above-mentioned flexible plastic bags and such, before the treatment, and then, the two are mixed together in sterile conditions at the start of peritoneal dialysis. To achieve this, a flexible plastic bag as disclosed in Unexamined Published Japanese Patent Application No. (JP-A) Sho 63-19149, which comprises two compartments separated by a removable partition, is suitably used.

Alternatively, a connector for mixing is installed in the peritoneal dialysis circuit, and the carbonyl compound-trapping agent can be infused through the connector.

This type of preparation procedure for peritoneal dialysates can be used to prepare heat-stable carbonyl compound-trapping agents as well as heat-unstable carbonyl compound-trapping agents.

Further, when peritoneal dialysis is conducted by circulating the peritoneal dialysate in a closed circuit with a small circulating pump, a filter device filled with the carbonyl compound-trapping agent may be installed anywhere in the circuit.

The peritoneal dialysate of the present invention can be used for a peritoneal dialysis treatment similar to a treatment using currently used peritoneal dialysates. Specifically, a suitable amount of the inventive peritoneal dialysate is infused into the peritoneal cavity of a patient, and low-molecular weight constituents present in the body are allowed to transfer into the peritoneal dialysate through the peritoneum. The peritoneal dialysate is circulated intermittently, and the treatment is further continued depending on the symptoms of the patient. During this period, the carbonyl compounds, as well as other substances such as creatinine, inorganic salt, and chloride ion, transfer to the peritoneal dialysate from blood and from inside the peritoneum. At the same time, the toxic activity of carbonyl compounds is eliminated by the carbonyl compound-trapping agent, thereby rendering the compounds harmless.

BEST MODE FOR CARRYING OUT THE INVENTION

The present invention is illustrated more specifically below with reference to examples, but is not to be construed as being limited thereto.

EXAMPLE 1

Measurement of the Amount of Carbonyl Compounds Present in the Peritoneal Dialysate and Peritoneal Dialysate Effluent In order to demonstrate the generation of carbonyl stress in the peritoneal cavity, the amount of carbonyl compounds present in the peritoneal dialysate effluent was measured according to the following experiment method.

(i) Measurement of Carbonyl Compounds

After the peritoneal dialysate (Baxter Ltd.; Dianeal PD-2 2.5) had been administered to a peritoneal-dialysis patient and had been allowed to dwell in the peritoneal cavity overnight, the peritoneal dialysate effluent was collected from the patient. Aliquots (400 $\mu$l) of both the peritoneal dialysate and the peritoneal dialysate effluent were separately mixed with a 400-µl solution of 0.5 N hydrochloric acid containing 1.5 mM 2,4-dinitrophenylhydrazine (2,4-DNPH) (Wako Pure Chemical Industries, Ltd.), and the mixture was stirred at room temperature for 30 minutes to react the carbonyl compound with 2,4-DNPH. Subsequently, an aqueous solution of 1 M acetone (40 µl) was added to the mixture, which was then stirred at room temperature for 5 minutes to remove excess 2,4-DNPH. The mixture was washed three times with 400 µl of n-hexane. The aqueous layer was recovered and the absorbance thereof was measured at 360 nm in a spectrophotometric microplate reader (Nippon Molecular Devices Co.; SPECTRAmax250).

(ii) Preparation of Calibration Curve

Aqueous solutions of various glucose concentrations were prepared and the amounts of carbonyl compounds derived from glucose were measured by the same method as described in (i). A calibration curve of glucose concentration vs. concentration of carbonyl compound was prepared based on this experiment.

(iii) Quantification of Carbonyl Compounds

Respective glucose concentrations of the peritoneal dialysate and peritoneal dialysate effluent were measured by using a glucose assay kit (Wako Pure Chemical Industries, Ltd.; Glucose CII-Test Wako). The amount of carbonyl compounds derived from glucose was estimated by using the calibration curve. The amount of carbonyl compounds in the fluids was determined by subtracting the amount of glucose-derived carbonyl compounds from the total amount of carbonyl compound in the sample solutions.

Figure 1:
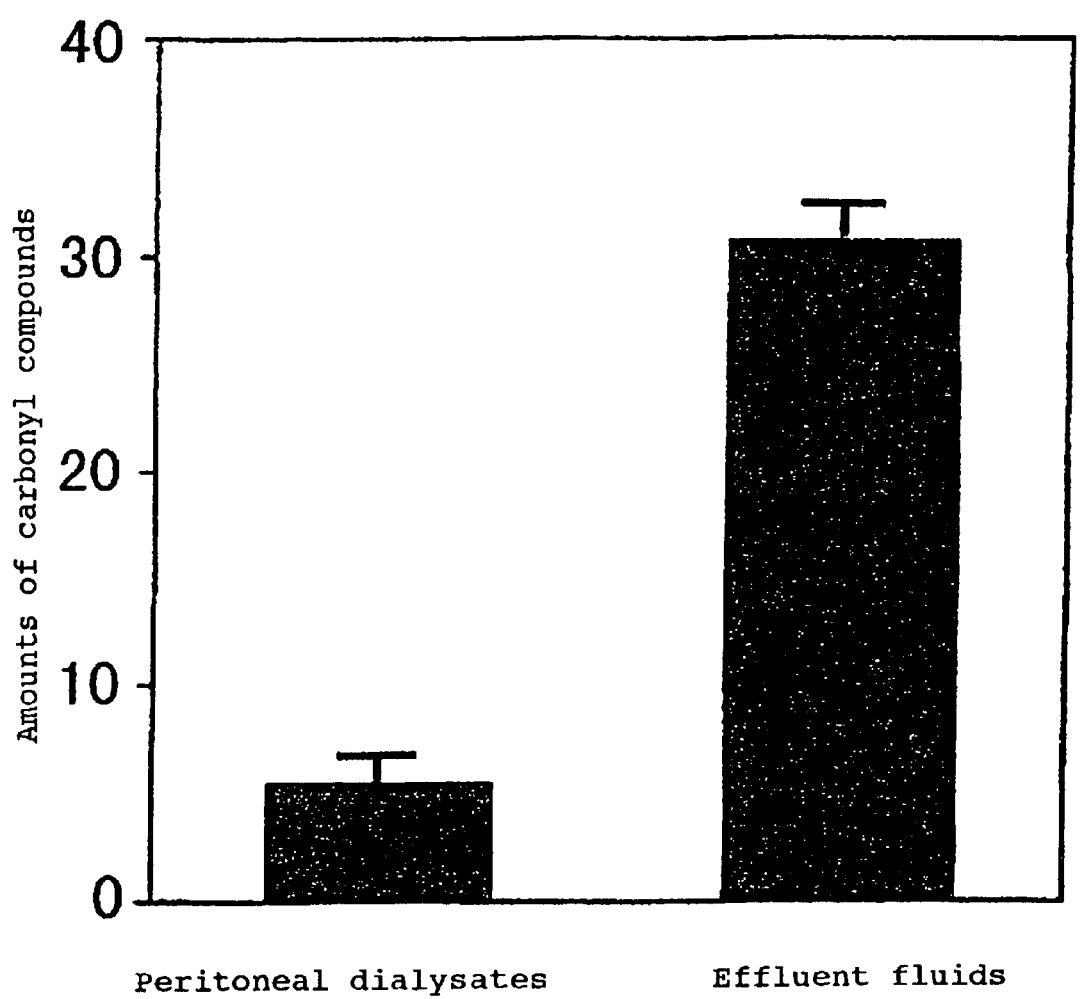
FIG. 1 shows the amounts of carbonyl compounds present in peritoneal dialysates and the effluent fluids.

The result obtained is shown in FIG. 1. The peritoneal dialysate effluent, which had dwelled overnight in the peritoneal cavity, contained five times more carbonyl compounds than the peritoneal dialysate prior to the administration did. This indicates the transfer of carbonyl compounds from the blood into the peritoneal cavity.

EXAMPLE 2

Histological Localization of Carbonyl-modified Proteins in the Peritoneum of a Peritoneal-dialysis Patient The localization of carbonyl compounds in peritoneal tissues of a peritoneal-dialysis patient was studied by immunostaining using malondialdehyde as the index.

Figure 2:
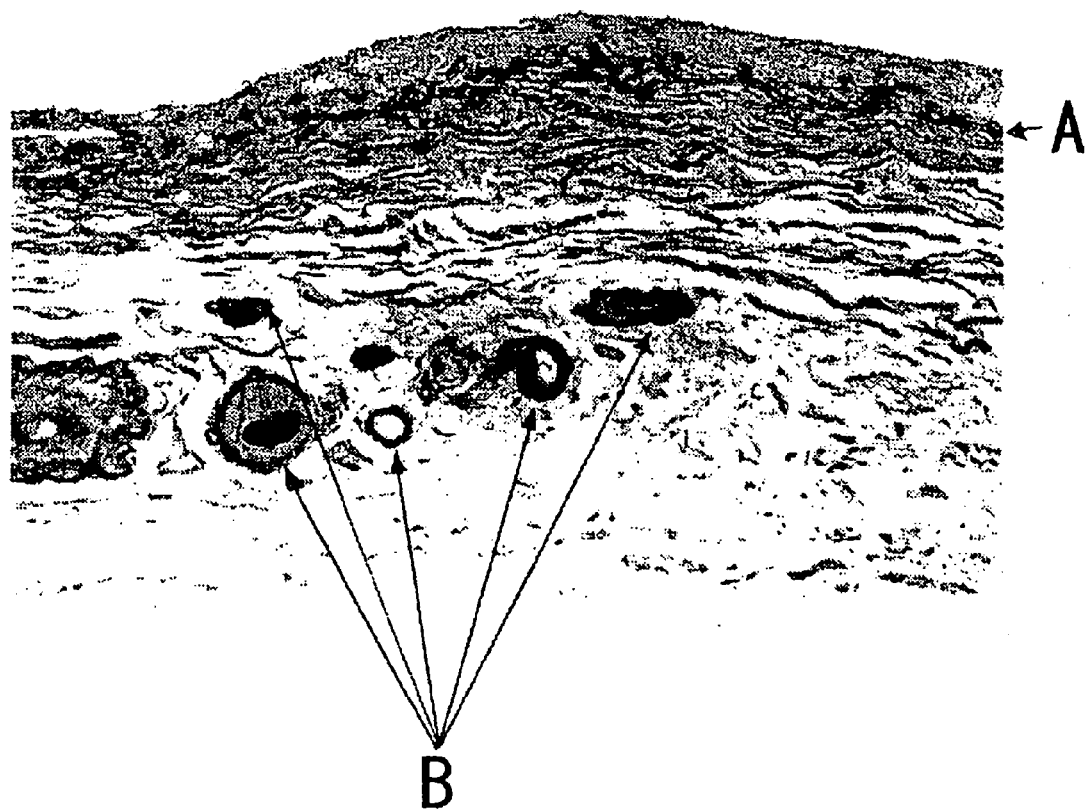
FIG. 2 shows a photograph of histological localization of carbonyl-modified proteins in the peritoneal tissue of a peritoneal-dialysis patient (in the top panel) and the corresponding schematic illustration (in the bottom panel). In this figure, A indicates positive areas in the connective tissues, on which mesothelial cells had been present but have been removed; B indicates positive areas on the thickened vascular wall.
Figure 2:
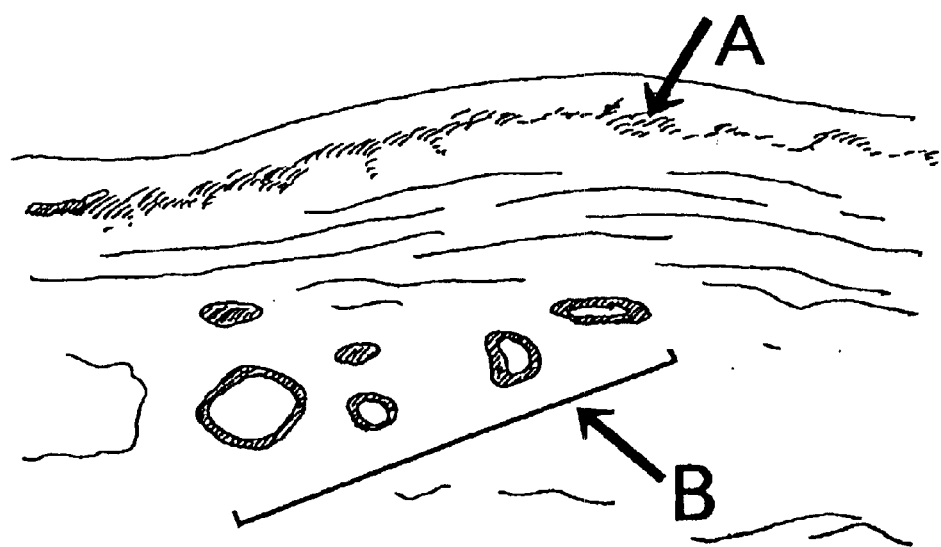

Peritoneal tissues from a peritoneal-dialysis patient (50-year-old male with a five-year history of peritoneal dialysis) were processed by immunostaining according to the method of Horie et al. (Horie, K. et al., J. Clin. Invest., 100, 2995–3004 (1997)). The primary antibody used was a mouse anti-malondialdehyde monoclonal antibody. The results showed that intense positive signals were present in the connective tissue under removed mesothelial cells, and the signals were also present on the thickened vascular wall (FIG. 2).

Malondialdehyde (MDA) is a carbonyl compound, which is generated by the degradation of peroxide lipid. Therefore, immunostaining was carried out by using antibodies against 4-hydroxy-2-nonenal, a degradation product of peroxide lipid other than MDA, and against carboxymethyllysine and pentosidine, which are generated by the oxidation of saccharides. The results showed that the positive signals were localized in the same areas as those shown in FIG. 2. These indicate that, in the peritoneal tissues of peritoneal-dialysis patients, proteins are modified in association with the enhancement of carbonyl stress caused by the presence of degradation products of peroxide lipids and carbonyl compounds generated by the oxidation of saccharides.

EXAMPLE 3

Peritoneal Cell Damages by Methylglyoxal

Decreased ultrafiltration of peritoneum by long-term peritoneal dialysis has been taken as evidence for an augmentation of the peritoneal surface area available for diffusive exchange (Krediet R T, Kidney Int, 55: 341–356 (1999); Heimburger O et al., Kidney Int, 38: 495–506 (1990); Imholz A L et al., Kidney Int, 43: 1339–1346 (1993); Ho-dac-Pannekeet M M et al., PeritDial Int, 17:144–150 (1997)). Namely, glucose in peritoneal dialysate flows out of peritoneal cavity by diffusion, thereby decreasing the dialytic function according to osmotic pressure gradient. An increased vascular surface area within the peritoneum might also account for this. In addition, the vascular endothelial growth factor (VEGF) might play a critical role in this pathology. VEGF increases vascular permeability (Senger D R et al., Science 219: 983–985 (1983); Connolly D T et al., J Biol Chem, 264: 20017–20024 (1989)), stimulates nitric oxide (NO) synthesis and vasodilation (Hood J D et al., Am J Physiol, 274: H1054–1058 (1998)), and induces inflammatory responses (Clauss M et al., J Exp Med, 172: 1535–1545 (1990); Melder R J et al., Nat Med, 2: 992–997 (1996)). Furthermore, VEGF is a powerful angiogenic factor contributing to the recovery from vascular lesions (Thomas K A, J Biol Chem, 271: 603–606 (1996); Ferrara N et al., Endocr Rev, 18: 4–25 (1997); Shoji M et al., Am J Pathol, 152: 399–411 (1998)). Consequently, effects of glucose degradation products contained in dialysate on VEGF production were examined.

<3-1>

VEGF Expression in Peritoneum Mesothelial and Vascular Endothelial Cells Cultured in the Presence of Glucose Degradation Products Peritoneum was obtained from 6-week-old male CD (SD) IGS rats (Charles-River, Kanagawa, Japan). Mesothelial cells were isolated based on the method of Hjelle et al. (Hjelle J T et al., Perit Dial Int, 9: 341–347 (1989)) and cultured in Dulbecco's modified Eagle's medium (DMEM) containing 10% fetal bovine serum. The mesothelial cells at passage 7 to 10 were cultured for 3 hours in a $CO_2$ incubator in the presence of various concentrations of glucose degradation products (glyoxal, methylglyoxal (Sigma, St. Louis, Mo.), or 3-deoxyglucosone (kindly provided from Fuji Memorial Research Institute, Otsuka Pharmaceutical Co., Kyoto, Japan). The expression of VEGF mRNA was analyzed by semiquantitative RT-PCR. Total RNA was isolated from the mesothelial cells using Rneasy Mini Kit (Qiagen, Germany). Five micrograms of the RNA was reverse-transcribed using oligo(dT)$_{12-18}$ primers (Gibco BRL, Gaithersburg, Md.) with 200 units of RNase H-free reverse transcriptase (Superscript II: Gibco BRL) and PCR amplification was performed as described previously (Miyata T et al., J Clin Invest, 93: 521–528 (1994)). The sequences of the primers used for the amplification of rat VEGF were 5'-ACTGGACCCTGGCTTTACTGC-3' (SEQ ID NO: 1) and 5'-TTGGTGAGGTTTGATCCGCATG-3' (SEQ ID NO: 2). The amplified product was 310 bp long. The primers used for the amplification of rat glyceraldehyde-3-phosphate dehydrogenase (G3PDH) were 5'-CCTGCACCACCAACTGCTTAGCCC-3' (SEQ ID NO: 3) and 5'-GATGTCATCATATTTGGCAGGTT-3' (SEQ ID NO: 4) and amplified a 322 bp fragment. The G3PDH served as an internal RNA control to allow comparison of RNA levels among different specimens. Specimens were amplified in a DNA Thermal cycler (Perkin Elmer Cetus, Norwork, Conn.) to determine the suitable number of cycles consisting of 0.5 min at 94° C., 1 min at 60° C., and 1.5 min at 72° C. In preliminary experiments, reverse transcription and PCR amplification were performed on various amounts of RNA for 16, 18, 21, 25, 28, 31, and 34 cycles. These experiments showed that, with 30 cycles of amplification for VEGF mRNA and with 21 cycle of G3PDH mRNA amplification, PCR product signals were quantitatively related to input RNA. PCR products resolved by electrophoresis in 1.5% agarose gel and stained with ethidium bromide were quantified by measuring the signal intensity with a quantification program (NIH image). Experiments were performed for each glucose degradation product concentration. Messenger RNA was determined in triplicate and the results were averaged for each experiment. A total of 3 to 4 independent experiments were performed for each experimental condition. The results were averaged and expressed as mean±S.D. The statistical significance was evaluated by an analysis of variance (ANOVA). If a significant difference was indicated by this analysis, results obtained with different concentrations of methylglyoxal were compared by Scheffe's t-test.

Figure 3:
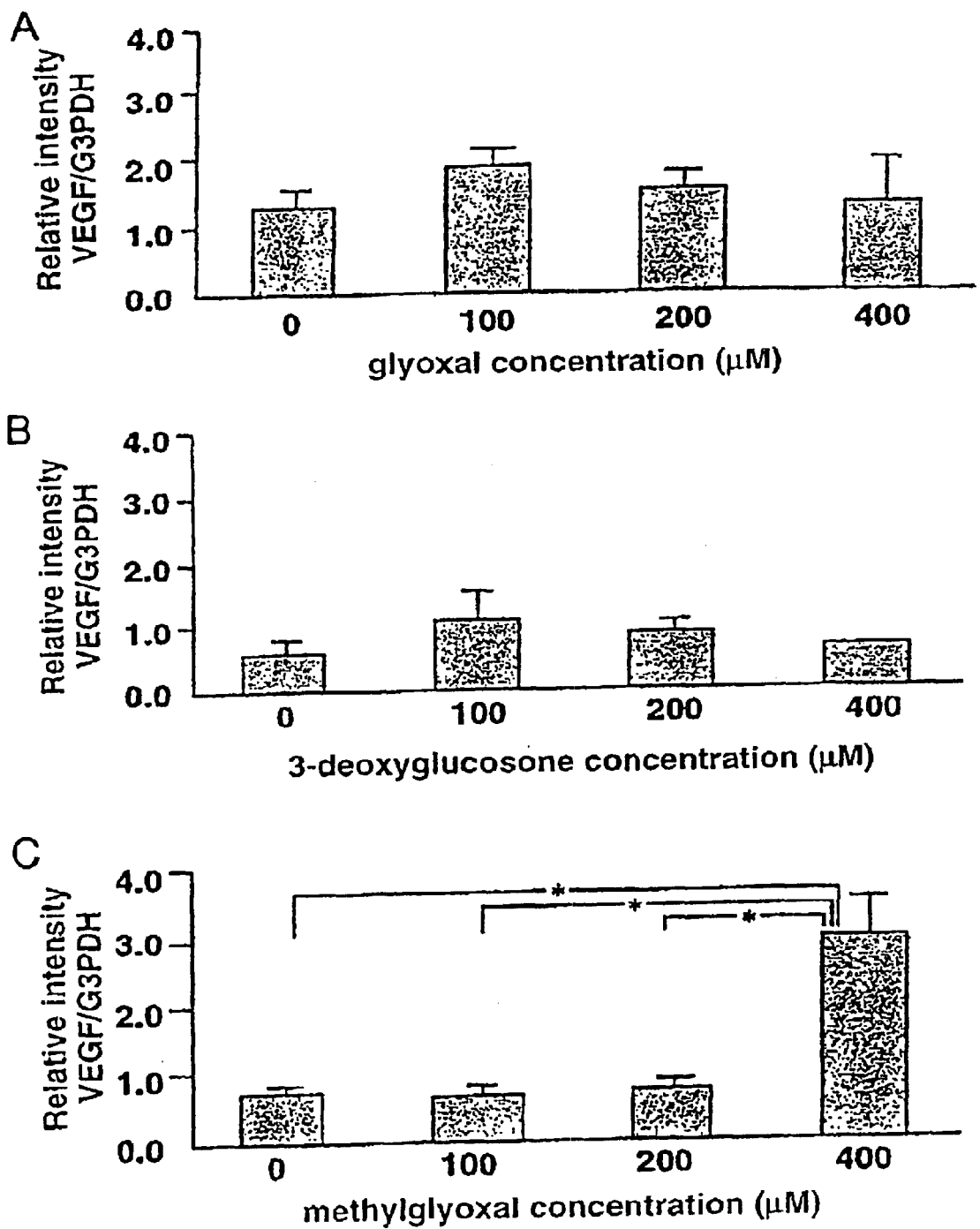
FIG. 3 shows VEGF mRNA expression in mesothelial cells exposed to glyoxal, methylglyoxal, and 3-deoxyglucosone. Reverse transcription was performed on total RNA from cultured rat mesothelial cells incubated with various concentrations (0, 100, 200, and 400 $\mu$M) of glyoxal (A), 3-deoxyglucosone (B), or methylglyoxal (C). VEGF and G3PDH cDNAs were amplified by PCR for 30 and 21 cycles, respectively. Experiments were performed in triplicate to calculate averages. Ratio of VEGF mRNA to G3PDH mRNA was calculated for the average of each experiment. The average±S.D. of the three experiments is illustrated in the figure. *$P<0.0005$.

At concentrations varying from 0 to 400 $\mu$M, neither glyoxal nor 3-deoxyglucosone modified VEGF expression (FIGS. 3A and 3B). Only methylglyoxal stimulated VEGF mRNA expression at a concentration of 400 $\mu$M (P<0.0005) (FIG. 3C). The sample RNAs that had not been reverse-transcribed did not yield the PCR product. All cells remained viable. Mesothelial cells were also cultured in the presence of higher concentrations of 3-deoxyglucosone (0.625, 2.5, and 5 mM), showing a decreased viability (cell viability was 80, 55, and 8% in the presence of 0.625, 2.5, and 5 mM 3-deoxyglucosone, respectively). Because of the decreased viability, VEGF mRNA expression could not be measured. As a consequence of these observations, only methylglyoxal was used in the subsequent experiments.

The release of VEGF protein into the culture supernatant was measured by ELISA for mesothelial cells cultured for 24 hours in the presence of various concentrations of methylglyoxal. Human microvascular endothelial cells were purchased from Kurabo (Osaka, Japan) and cultured in VEGF-depleted EGM-2 medium (Takara, Tokyo, Japan). The cells were incubated with methylglyoxal in the same manner as rat peritoneum mesothelial cells. The VEGF protein in the culture supernatant prepared in duplicate was quantified by enzyme-linked immunosorbent assay (ELISA) using a kit (Quantikine: R&D Systems, Minneapolis, USA) according to the attached manual. The experiment was repeated three times. The results were statistically analyzed as described above.

Figure 4:
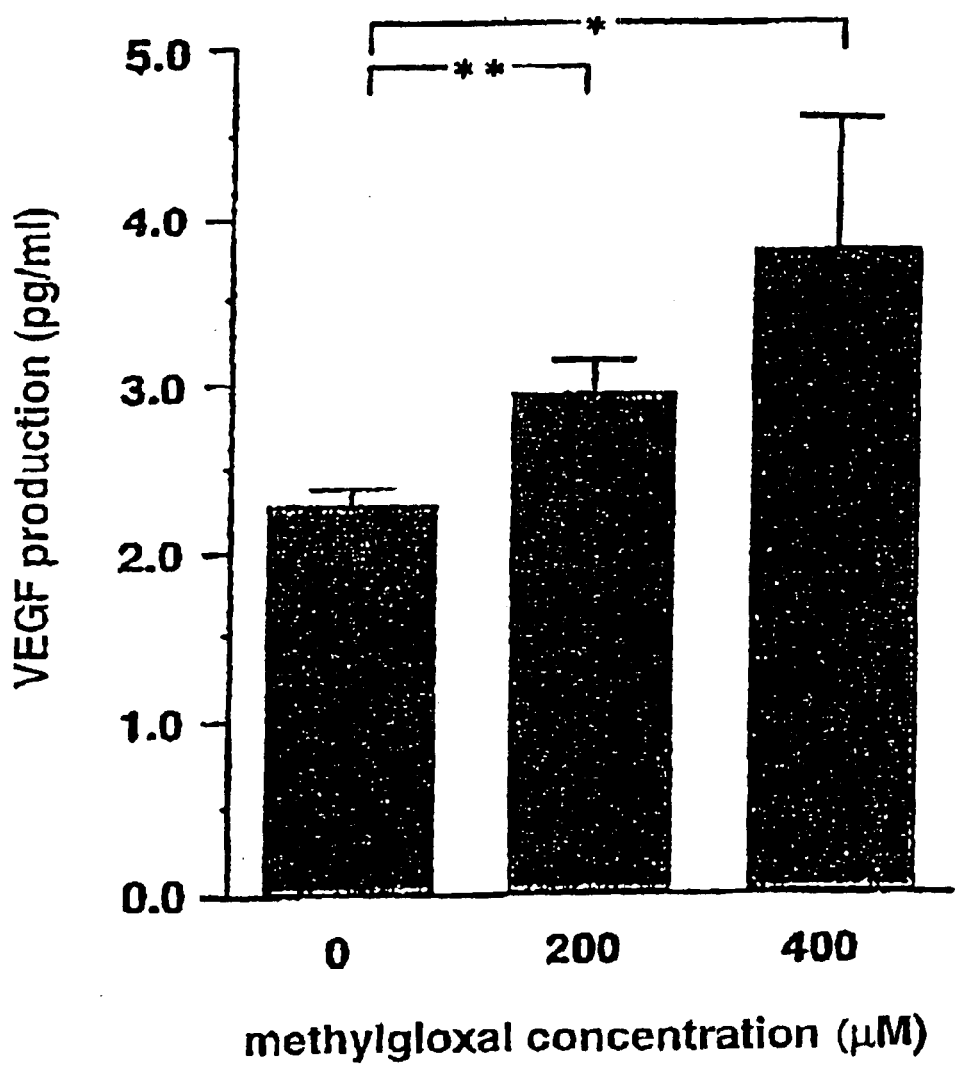
FIG. 4 shows VEGF protein production in microvascular endothelial cells exposed to methylglyoxal. Human endothelial cells were cultured in the presence of various concentrations (0, 200, and 400 $\mu$M) of methylglyoxal, and VEGF protein released into culture supernatant was quantified by ELISA. Representative data from the three experiments are shown. The data are expressed as mean±range. *$P<0.05$, and **$P<0.01$.

As a result, addition of methylglyoxal to the medium resulted in a dose-dependent increase of VEGF (FIG. 4). No VEGF release was detected during in the absence of methylglyoxal. Namely, at protein level, methylglyoxal also dose-dependently stimulates the production and release of VEGF.

Figure 5:
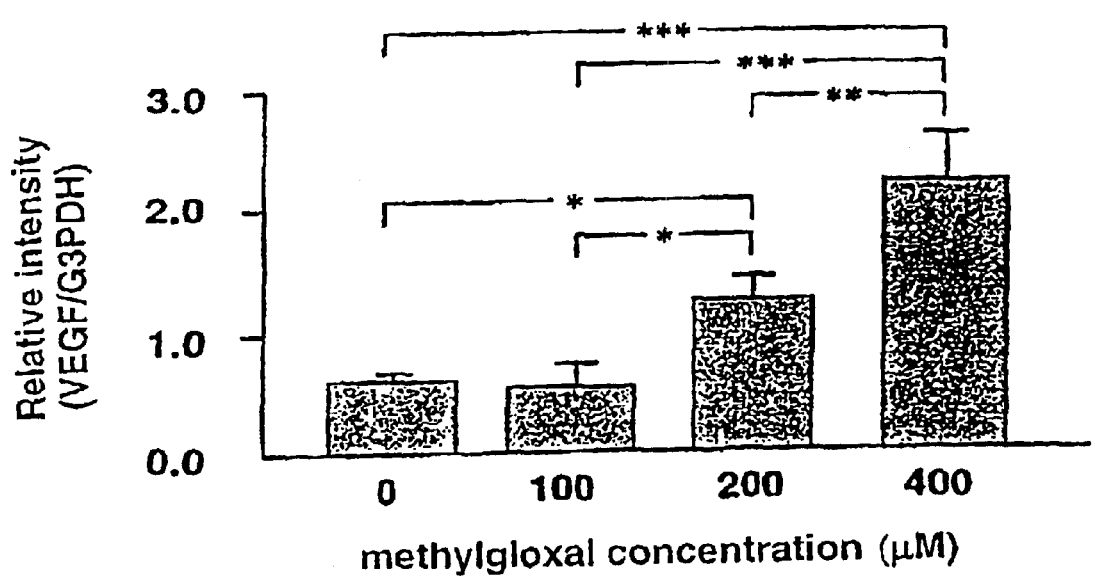
FIG. 5 shows VEGF mRNA expression in endothelial cells exposed to methylglyoxal. Human endothelial cells were cultured in the presence of various concentrations (0, 100, 200, and 400 $\mu$M) of methylglyoxal. VEGF and G3PDH cDNAs were amplified by PCR for 30 and 21 cycles, respectively. Experiments were performed in triplicate to calculate mean values. Ratio of VEGF mRNA to G3PDH mRNA was calculated for the mean of each experiment. The mean±S.D. of the three experiments is illustrated in the figure. *$P<0.05$, $P<0.005$, and *$P<0.0001$.

VEGF mRNA expression was then assessed in endothelial cells cultured in the presence of various concentrations (0 to 400 $\mu$M) of methylglyoxal. Experiments were performed as those for rat mesothelial cells. However, primers used for human VEGF amplification were 5'-GGCAGAATCATCACGAAGTGGTG-3' (SEQ ID NO: 5) and 5'-CTGTAGGAAGCTCATCTCTCC-3' (SEQ ID NO. 6). The amplified fragment was 271 bp long. The same primers were used for human and rat G3PDH amplifications. The analyses revealed that VEGF mRNA expression rose in a dose-dependent manner (FIG. 5).

<3-2>
VEGF Expression in Peritoneal Tissues of Rats Given Intraperitoneal Injection of Methylglyoxal To further assess the biological effects of methylglyoxal on VEGF mRNA expression in the peritoneum in vivo, rats were given various amounts of methylglyoxal into their peritoneal cavity for 10 days. Six-week-old male CD (SD) IGS rats were given a daily intraperitoneal injection of 50 ml/kg of a saline solution containing various concentrations of methylglyoxal for 10 days. Peritoneum was isolated from the parietal walls and investigated for VEGF mRNA expression. Experiments were performed as the above-mentioned in vitro experiments for rat mesothelial cells. However, mRNA was extracted from peritoneal tissues with ISOGEN (Nippon Gene, Tokyo, Japan). In addition, PCR amplification was performed for 28 cycles for VEGF mRNA and for 16 cycles for G3PDH mRNA.

Figure 6:
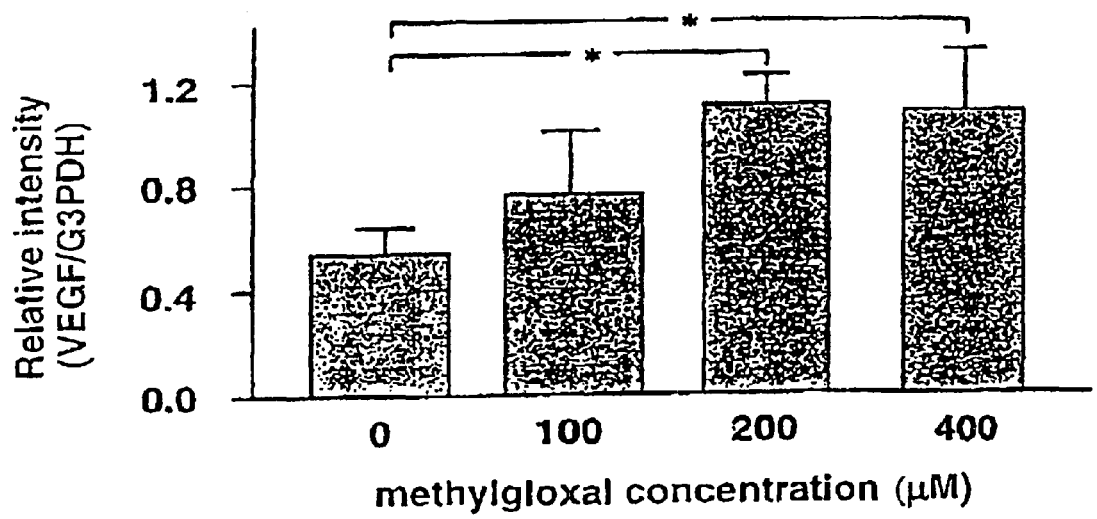
FIG. 6 shows VEGF mRNA expression in peritoneal tissues of rats given daily intraperitoneal loads of methylglyoxal for 10 days. VEGF and G3PDH mRNA expressed in peritoneums were amplified by RT-PCR for 28 and 16 cycles, respectively. Experiments were performed in triplicate to calculate mean values. Ratio of VEGF mRNA to G3PDH mRNA was calculated for the mean of each experiment. The mean±S.D. of the three experiments is illustrated in the figure. *$P<0.05$.
Figure 7:
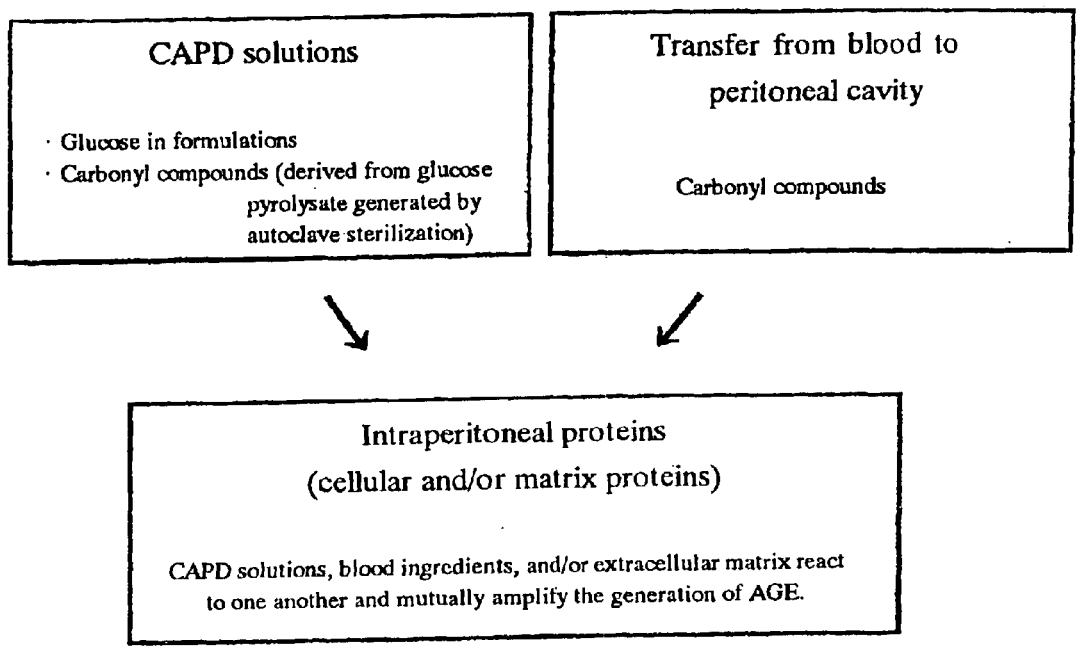
FIG. 7 shows the generation process of carbonyl stress in the peritoneal cavity of peritoneal-dialysis patient.

As shown in FIG. 6, VEGF mRNA expression in samples of the parietal peritoneum increased significantly (P<0.05) according to methylglyoxal concentration. On optical microscopy, the peritoneal tissue was unaffected: the number of vessels, the vascular wall, the interstitium, and mesothelial cells remained normal.

<3-3>
VEGF and Carboxymethyllysine (CML) Immunostaining of Peritoneal Tissue of Long-term Peritoneal Dialysis Patients The distribution of VEGF and carboxymethyllysine was examined by immunohistochemistry in the peritoneal tissues of nine peritoneal dialysis patients. Carboxymethyllysine is derived from glucose degradation products such as glyoxal and 3-deoxyglucosone (Miyata T et al., Kidney Int, 55:389–399 (1999)). An anti-carboxymethyllysine antibody was therefore used as a marker of glucose degradation product-modified proteins.

Peritoneal tissues were isolated, after obtaining informed consent, from nine non-diabetic peritoneal dialysis patients during catheter reinsertion (Table 1). Reinsertion was necessitated by catheter failure due to damage, incorrect position, and/or obstruction. No patients suffered from peritonitis. Normal peritoneal tissue was obtained, during abdominal surgery, from two male subjects (48 and 58 years old) with normal renal function.

Two-$\mu$-thick peritoneal tissue sections were mounted on slides coated with 3-aminopropyltriethoxy silane (Sigma), deparaffined, rehydrated in distilled water, and incubated with a buffer solution (0.05 M Tris-HCl (pH 7.2), 0.1 M NaCl) containing Pronase (0.5 mg/$\mu$l: Dako, Glostrup, Denmark) for 15 min at room temperature. The slides were washed with PBS containing 0.5% Tween 20, blocked in 4% skim milk for 2 hours, and subsequently incubated with anti-VEGF rabbit IgG (Santa Cruz Biotechnology, Santa Cruz, Calif.) or anti-AGE mouse IgG (Ikeda K et al., Biochemistry, 35: 8075–8083 (1996)), the epitope of which was carboxymethyllysine (Miyata T et al., Kidney Int, 51: 1170–1181 (1997)), overnight in humid chambers at 4° C. The sections were washed and incubated with 1:100 diluted goat anti-rabbit IgG conjugated with peroxidase or goat anti-mouse IgG conjugated with peroxidase (Dako) for 2 hours at room temperature, followed by the detection with 3,3'-diaminobenzidine solution containing 0.003% $H_2O_2$. Periodic acid-Schiff staining was also performed for histological analysis. Immunostaining was independently evaluated for signal intensity and distribution by two observers.

Results are shown in Table 1. In the table, "normal1" and "normal2" indicate samples derived from the subjects with normal renal function and "PD1" to "PD9" indicate samples derived from peritoneal dialysis patients. In the pictures of the peritoneal tissue of a representative long-term peritoneal dialysis patient (PD6 in Table 1), interstitial fibrosis, and thickening and hyalinosis of vascular walls were observed. Both VEGF and carboxymethyllysine co-localized in the mesothelial cells and vascular walls. In mesothelial layer, the signal with VEGF was weaker than that with carboxymethyllysine. Results were similar for the eight other patients. In the normal peritoneal sample (normal2 in Table 1), in contrast with peritoneal dialysis samples, VEGF was present only in the vascular walls but was absent in the mesothelial layer. Carboxymethyllysine was absent in the mesothelial layer and the signal was very weak in the vascular walls. Observations were similar in another control normal sample. No immunostaining was observed when normal mouse IgG was used. Thus, the fact that VEGF expression in the mesothelial layers and its co-localization with carboxymethyllysine are observed only in peritoneal dialysis patients suggests that the glucose degradation products present in peritoneal dialysate actually enhance VEGF production in uremic patients through peritoneal dialysis.

fluid at a final concentration of 0, 1, 10, or 100 mM. The mixture was incubated at 37° C. The incubation period was 1 to 2 when assaying pentosidine, and 2 weeks when assaying protein carbonyl. The quantitative assay for pentosidine was performed using HPLC (SHIMADZU Co.; LC-10A) after the hydrolysis of proteins in 6 N HCl at 110° C. (T. Miyata et al., 1996, J. Am. Soc. Nephrol, 7:1198–1206; T. Miyata et al., 1996, Proc. Natl. Acad. Aci. USA, 93:2353–2358). The quantitative determination of protein carbonyl was carried out by measuring the absorbance (Nippon Molecular Devices Co.; SPECTRAmax 250) of hydrazone generated by the reaction of a carbonyl group after incubation with 2,4-dinitrophenylhydrazine (2,4-DNPH; Wako Pure Chemical Industries, Ltd.) (Levine, R. L. et al., Methods Enzymol., 233, 346–357 (1994)).

Figure 8:
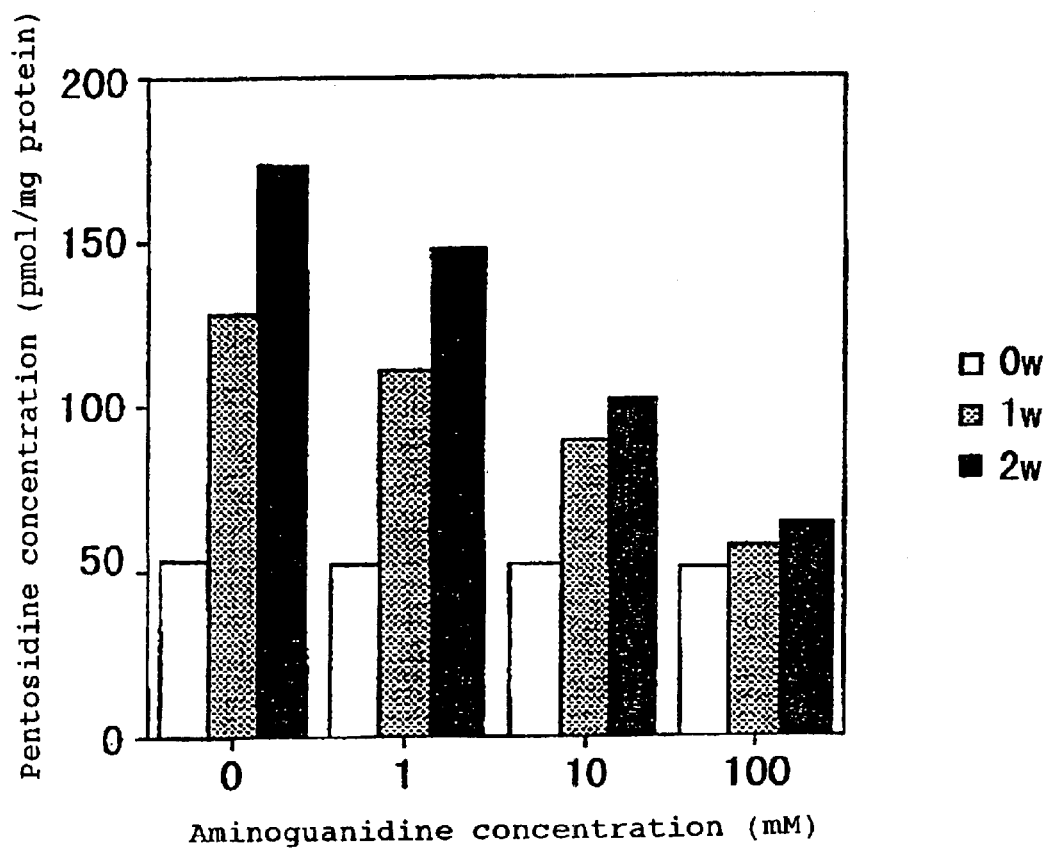
FIG. 8 shows the effect of the addition of aminoguanidine on the generation of pentosidine following the incubation of the peritoneal dialysis effluent.
Figure 9:
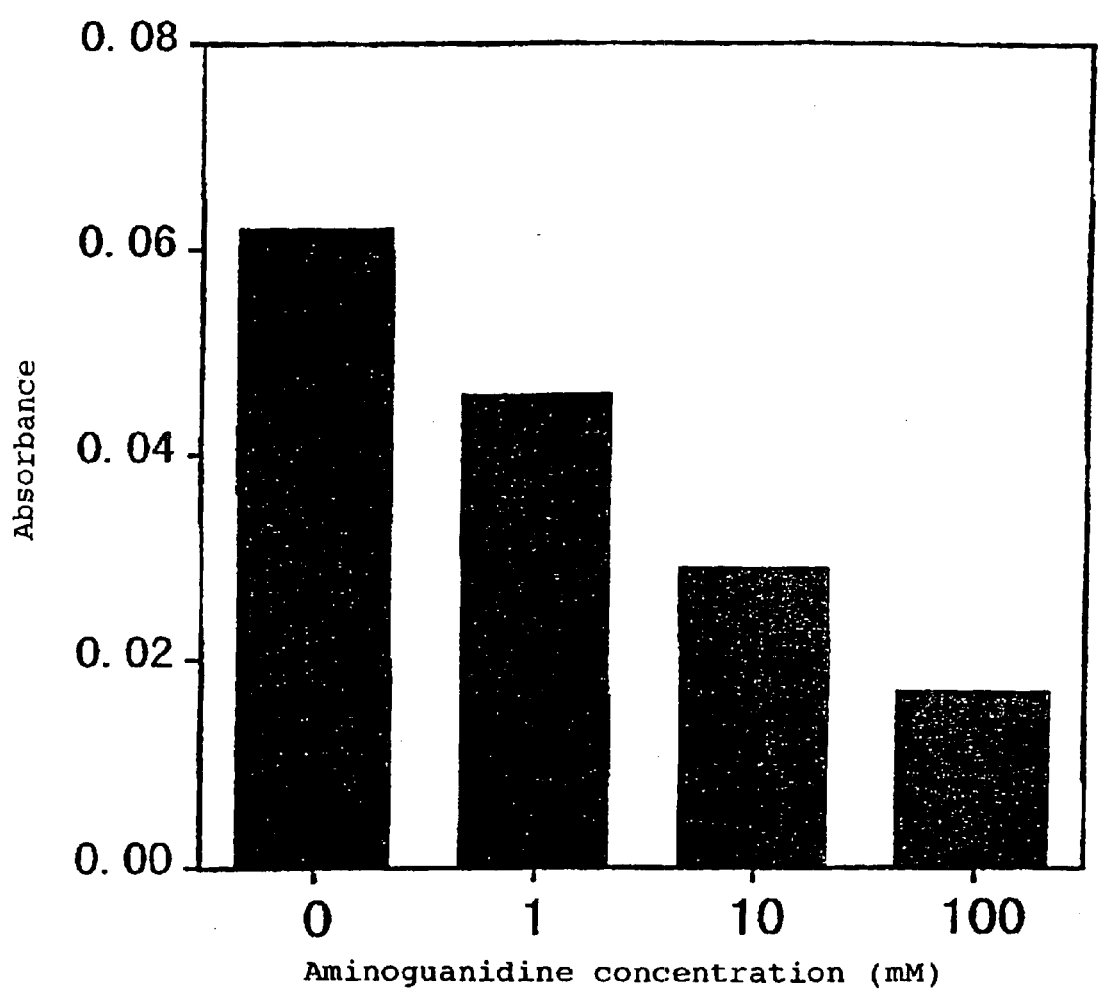
FIG. 9 shows the effect of the addition of aminoguanidine on the generation of protein carbonyl following the incubation of the peritoneal dialysis effluent.

Based on the experimental result, aminoguanidine was shown to inhibit the generation of pentosidine in a concentration-dependent manner (FIG. 8). Aminoguanidine exhibited a similar inhibiting effect on the generation of protein carbonyl in a concentration-dependent manner (FIG. 9).

TABLE 1

Immunohistochemical detection of CML and VEGF in peritoneal tissues of PD patients

| Samples | Gender | Age (yr) | PD duration (months) | CML mesothelial layer | CML vascular walls | VEGF mesothelial layer | VEGF vascular walls |
|---|---|---|---|---|---|---|---|
| normal1 | M | 48 | – | – | ± | – | + |
| normal2 | M | 58 | – | – | ± | – | + |
| PD1 | F | 53 | 3 | + | + | + | + |
| PD2 | M | 44 | 4 | + | + | + | + |
| PD3 | M | 43 | 45 | + | + | + | + |
| PD4 | F | 54 | 60 | ++ | ++ | ++ | + |
| PD5 | M | 52 | 70 | ++ | ++ | + | + |
| PD6 | M | 51 | 90 | ++ | ++ | ++ | ++ |
| PD7 | M | 45 | 105 | ++ | ++ | ++ | ++ |
| PD8 | M | 62 | 108 | ++ | ++ | ++ | ++ |
| PD9 | M | 66 | 110 | ++ | ++ | ++ | ++ |

–: negative, ±: faint, +: positive, ++: strongly positive

The results mentioned above confirm that peritoneal dialysis patients are in carbonyl-stress state because of glucose degradation products or the like in peritoneal dialysate and further demonstrate for the first time that methylglyoxal enhances VEGF production in peritoneal cells. This suggests that at least a part of causes for decrease of peritoneal permeability by glucose degradation products contained in peritoneal dialysate is enhancement of VEGF production and angiogenic stimulation accompanied with it.

EXAMPLE 4
Effect of a Carbonyl Compound-trapping Agent Added to Dialysate Effluents from Peritoneal-dialysis Patients

<4-1>

Pentosidine is an AGE structure, which has been seen to accumulate 20 times more in the blood of patients with renal failure compared to normal healthy persons (Miyata, T. et al., J. Am. Soc. Nephrol., 7: 1198–1206 (1996)). The inventors tested how aminoguanidine addition influenced the increase of pentosidine and carbonyl group on proteins (protein carbonyl) when the fluid effluent from a peritoneal-dialysis patient was incubated at 37° C.

An effluent from a peritoneal-dialysis patient, which had been kept overnight, was centrifuged, and the resulting supernatant was sterilized by filtration (pore size; 0.45 μm). Aminoguanidine (Tokyo Kasei Kogyo Co.) was added to the

<4-2>

Next, aminoguanidine was tested for its effect on the amounts of carbonyl compounds other than glucose present in a fluid that was kept overnight in a peritoneal-dialysis patient, according to the following experiment method.

(A). Incubation of the Peritoneal Dialysate Effluent

The peritoneal dialysate effluent was recovered from the patient and filtered with a filter with a pore size of 0.45 μm. Aminoguanidine (Tokyo Kasei Kogyo Co.) was added to the fluid at a concentration of 0, 10, 50, or 250 mM to prepare a sample solution. An aliquot (1 ml) of the sample solution was added into a plastic tube with a screw cap, and the tube was incubated at 37° C. for 15 hours. The sample solutions were stored at −30° C. prior to the incubation.

(B) Quantification of Carbonyl Compounds (i) Assay for Carbonyl Compounds Present in Sample Solutions Each of 400-μl aliquots of sample solutions was mixed with a 400-μl solution of 0.5 N hydrochloric acid containing 1.5 mM 2,4-DNPH (Wako Pure Chemical Industries, Ltd.), and then, the mixture was stirred at room temperature for 30 minutes to react the carbonyl compound with 2,4-DNPH. Subsequently, an aqueous solution of 1 M acetone (40 μl) was added to the mixture. The resulting mixture was stirred at room temperature for 5 minutes to remove excess 2,4-DNPH by reacting it with acetone. The aqueous mixture was washed three times with 400 μl of n-hexane. The aqueous layer was recovered and the absorbance thereof was measured at 360 nm in a spectrophotometric microplate reader (Nippon Molecular Devices Co.; SPECTRAmax250).

(ii) Preparation of Calibration Curve

Aqueous solutions of various glucose concentrations were prepared and the amounts of carbonyl compounds derived from glucose were measured by the same method as described in (i); a calibration curve of glucose concentration vs. concentration of carbonyl compound was prepared based on this experiment.

(iii) Quantification of Carbonyl Compounds

Figure 10:
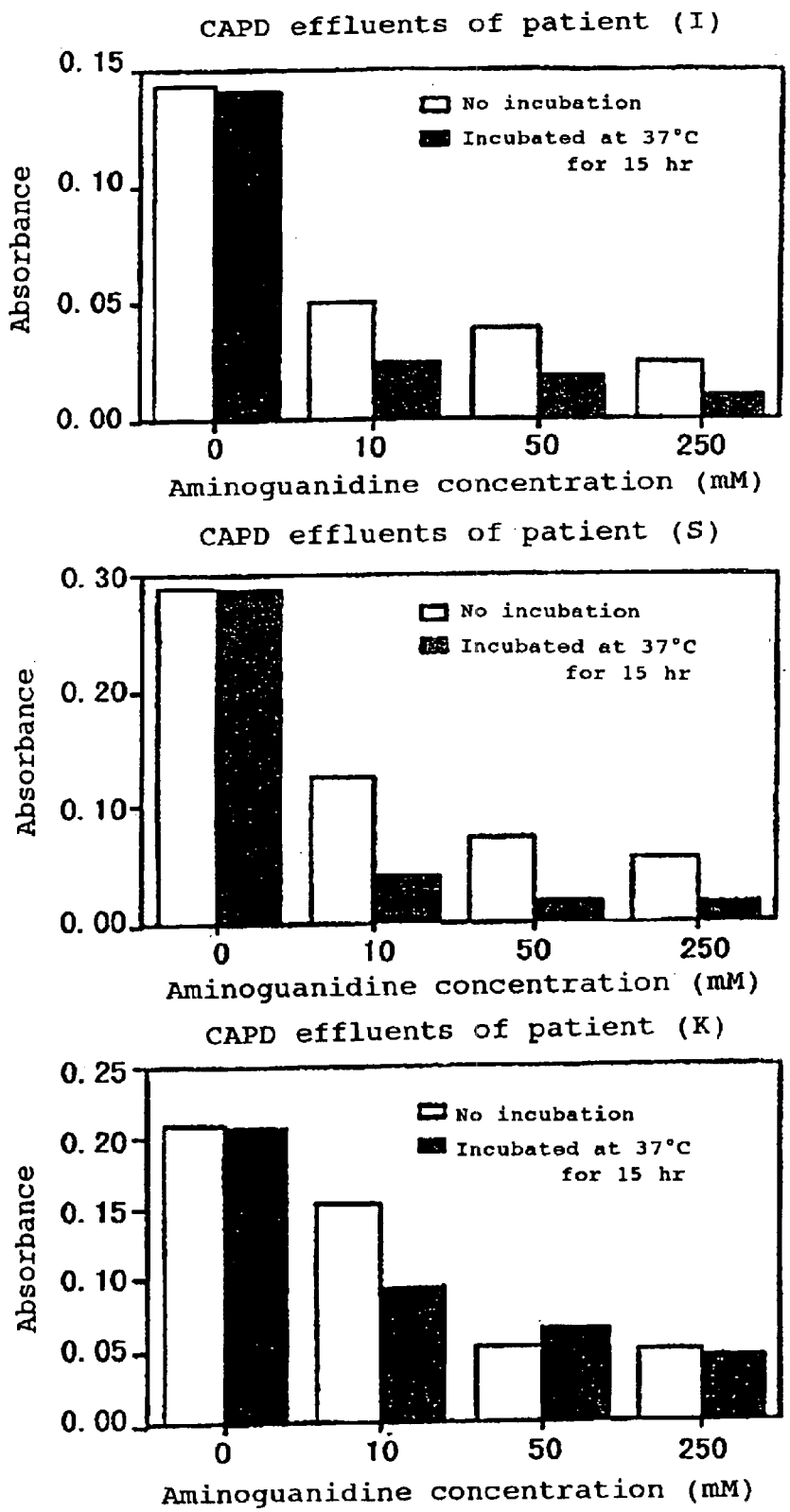
FIG. 10 shows the effect of the addition of aminoguanidine on the amounts of carbonyl compounds present in peritoneal-dialysis (CAPD) effluents from three peritoneal-dialysis patients (patient I, patient S, and patient K).

Respective glucose concentrations of the samples were determined by using a glucose assay kit (Wako Pure Chemical Industries, Ltd.; Glucose CII-Test Wako). The amount of carbonyl compounds derived from glucose was estimated by using the calibration curve. The amount of carbonyl compound in the sample was determined by subtracting the amount of glucose-derived carbonyl compounds from the total amount of carbonyl compounds in the sample solution. The result obtained is shown in FIG. 10. As the concentration of aminoguanidine increased, the amounts of carbonyl compounds other than glucose decreased, both in the unincubated and incubated (37° C. for 15 hours) samples.

These results showed that the addition of the carbonyl compound-trapping agent to the peritoneal dialysate or the administration of the trapping agent to patients is effective in inhibiting the generation and/or accumulation of carbonyl compounds in the peritoneal dialysate infused into the peritoneal cavity. Thus, carbonyl compounds derived from the peritoneal dialysate or from the blood are eliminated from the peritoneal cavity, thereby achieving the improvement of the carbonyl-stress state in peritoneal-dialysis patients.

EXAMPLE 5

Effect of a Carbonyl Compound-trapping Agent Added to the Peritoneal Dialysate in the Process of Heat Sterilization Peritoneal dialysates contain a high concentration of glucose as an osmoregulatory agent (1.35–4.0 w/v %). Glucose is unstable to heating and undergoes degradation during heat sterilization or storage. Degradation products of glucose have been reported to include 5-hydroxymethylfurfural (5-HMF), levulinic acid, and acetaldehyde (Richard, J. U. et al., Fund. Appl. Toxic., 4: 843–853(1984), Nilsson, C. B. et al., Perit. Dial. Int., 13: 208–213(1993)). The inventors tested aminoguanidine for its inhibiting effect on the generation of carbonyl compounds during heat sterilization of a peritoneal dialysate, by monitoring the quantities of 5-HMF and carbonyl compounds. Since the degree of glucose degradation is affected by pH of the solution, two peritoneal dialysates of acidic pH (pH 5.3) and neutral pH (pH 7.0) were prepared to carry out the experiment. Sterilization temperature was 121° C.

<5-1>

5-HMF was assayed by high performance liquid chromatography (SHIMADZU Co.; LC-10A) (Nilsson, C. B. et al., Perit. Dial. Int., 13: 208–213(1993)).

Figure 11:
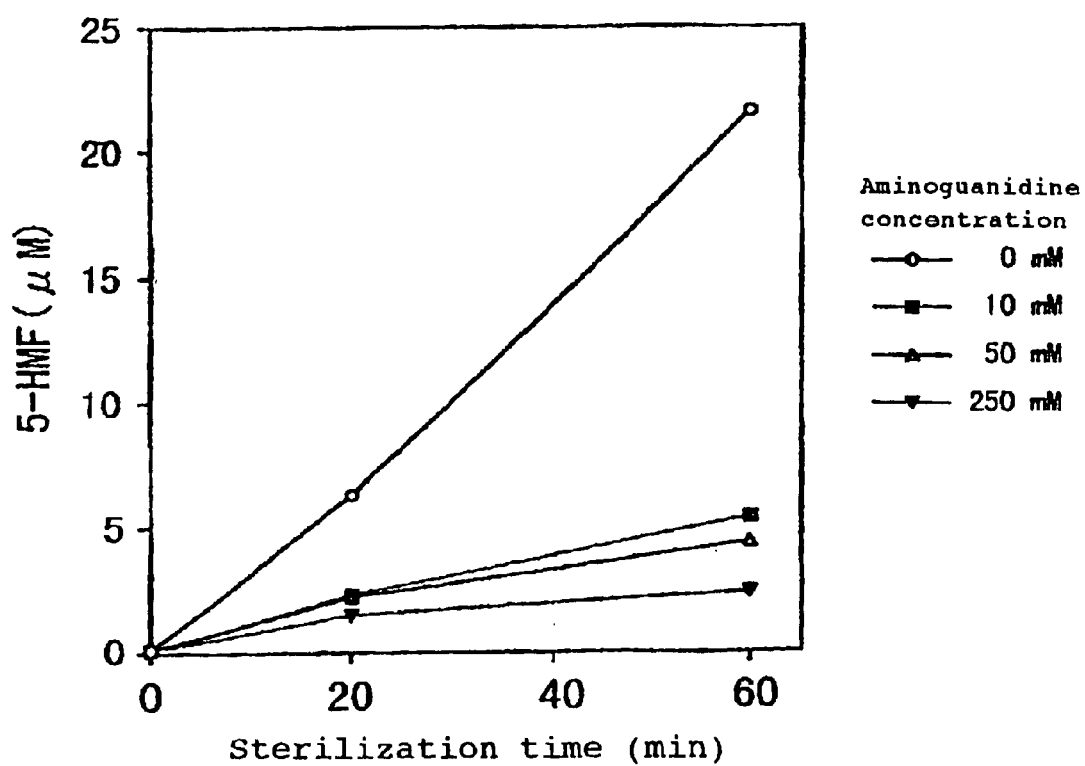
FIG. 11 shows the effect of the addition of aminoguanidine on the generation of 5-HMF within the peritoneal dialysate in an acidic pH range.
Figure 12:
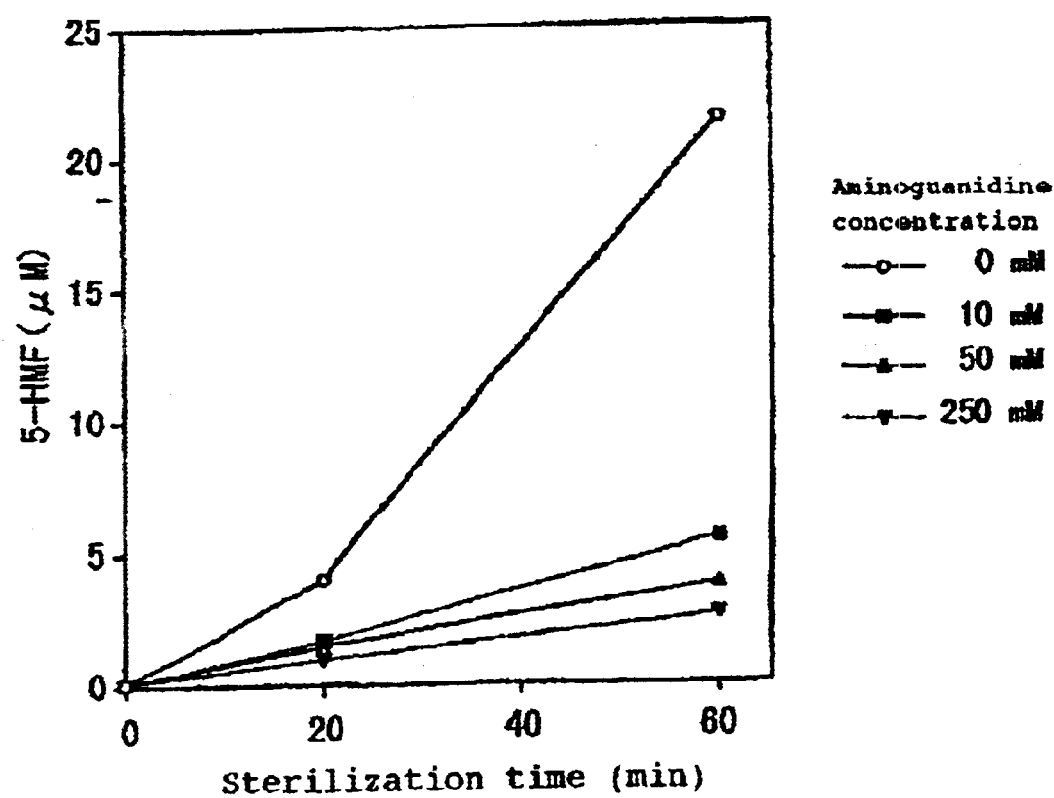
FIG. 12 shows the effect of the addition of aminoguanidine on the generation of 5-HMF within the peritoneal dialysate in a neutral pH range.

The results showed that aminoguanidine effectively inhibited the generation of 5-HMF in a concentration-dependent manner at both acidic pH (FIG. 11) and neutral pH (FIG. 12).

<5-2>

Quantification of carbonyl compounds in the peritoneal dialysate was carried out in the same manner as described in Example 1 by measuring the absorbance after the reaction with 2,4-DNPH (Levine, R. L. et al., Methods Enzymol., 233: 346–357 (1994)). Sterilization temperature was 121° C.

Figure 13:
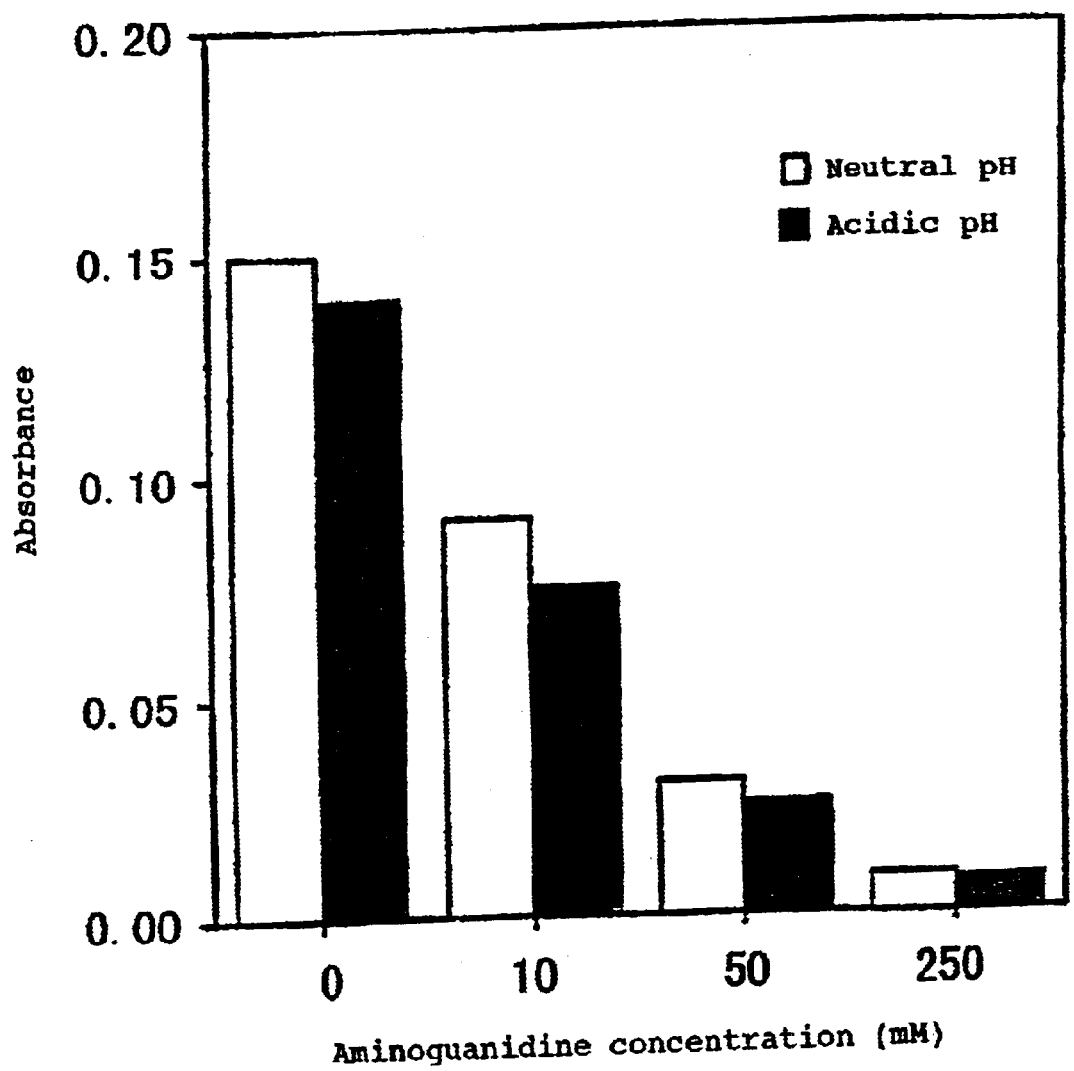
FIG. 13 shows the effect of the addition of aminoguanidine on the amounts of carbonyl compounds within the peritoneal dialysate in acidic and neutral pH ranges.

The result showed that aminoguanidine also effectively inhibited the generation of carbonyl compounds in a concentration-dependent manner (FIG. 13).

These findings clarified that the addition of an agent inhibiting the generation of carbonyl compounds to the peritoneal dialysate is highly effective in inhibiting the generation and/or accumulation of carbonyl compounds in the peritoneal dialysate.

EXAMPLE 6

Effect of Carbonyl Compound-trapping Beads Added to the Peritoneal Dialysate on the Generation of Pentosidine Carbonyl compound-trapping beads, which comprise sulfonylhydrazine group-bound crosslinked polystyrene resin (PS-TsNHNH$_2$; ARGONAUT TECHNOLOGIES CO.), were tested for the effect of eliminating carbonyl compounds from the peritoneal dialysate. The peritoneal dialysate, and the dialysate containing carbonyl compound-trapping beads, were incubated at 37° C. to evaluate the effect of inhibiting the generation of pentosidine. Dimethylsulfoxide (100 µl) was added to the tube containing carbonyl compound-trapping beads, to swell the beads. Then 800 µl of a peritoneal dialysate (Baxter Ltd.; Dianeal PD-4,1.5) and 200 µl of an aqueous solution of 150 mg/ml bovine serum albumin were added to the tube. The tube was incubated at 37° C. for 1 week. After the incubation, the beads were removed by using a centrifugal filter tube (Millipore Co.; UFC30GV00) having membrane pores of 0.22 µm. Next, 50 µl of 10% trichloroacetic acid was added to the solution (50 µl) from which the beads had been removed. The mixture was centrifuged to precipitate protein. The protein pellet was washed with 300 µl of 5% trichloroacetic acid, and then dried. Then, 100 µl of 6 N HCl was added to the protein pellet, and the dissolved protein was heated at 110° C. for 16 hours. The resulting sample was assayed for the quantification of pentosidine by HPLC (T. Miyata et al., 1996, J. Am. Soc. Nephrol., 7: 1198–1206; T. Miyata et al., 1996, Proc. Natl. Acad. Sic. USA, 93: 2353–2358).

Figure 14:
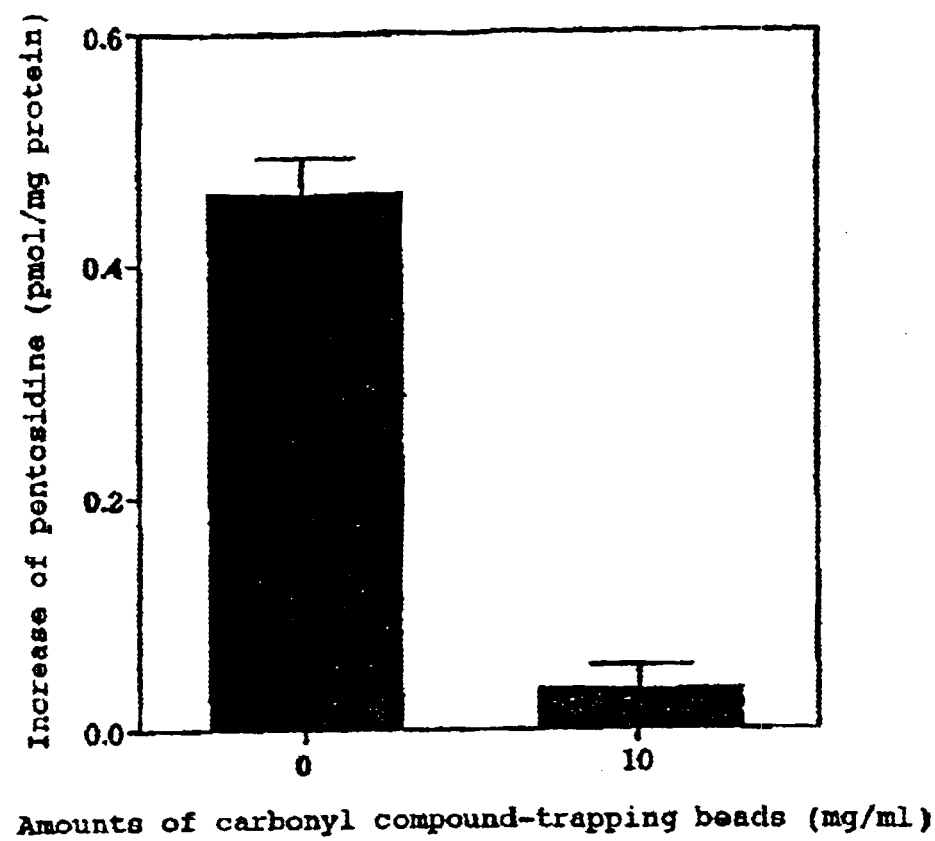
FIG. 14 shows the suppressing effect of carbonyl compound-trapping beads added to the peritoneal dialysate on the generation of pentosidine.

The amounts of pentosidine generated by the incubation at 37° C. are summarized in FIG. 14. It was revealed that the addition of carbonyl compound-trapping beads had a strong effect in inhibiting the generation of pentosidine.

EXAMPLE 7

Effect of the Elimination of Carbonyl Compounds by Carbonyl Compound-trapping Beads Added to the Peritoneal Dialysate Carbonyl compound-trapping beads were tested for the effect of eliminating carbonyl compounds from the peritoneal dialysate. Dimethylsulfoxide (100 µl) was added to a tube containing carbonyl compound-trapping beads (PS-TsNHNH$_2$; ARGONAUT TECHNOLOGIES CO.), to swell the beads. Then, 900 µl of a peritoneal dialysate (Baxter Ltd.; Dianeal PD-4,1.5) was added. The mixture was stirred at room temperature for 16 hours by using a rotator. Subsequently, the suspension containing the carbonyl compound-trapping beads was filtered with a centrifugal filter tube (Millipore Co.; UFC30GV00), having membrane pores of 0.22 µm, and the amount of carbonyl compounds in the filtrate was assayed by following method.

<Quantification of Carbonyl Compounds>

(1) Assay of Sample Solutions

A sample solution (200 µl) was mixed with 200 µl of a 0.5 N hydrochloric acid solution containing 2,4-DNPH (0.025%), and the mixture was incubated at 30° C. for 30 minutes. Subsequently, an aqueous solution of 1 M acetone (20 μl) was added to the mixture. The resulting mixture was incubated at 30° C. for 10 minutes. The aqueous mixture was washed 3 times with 200 μl of n-hexane, and 200μ of octanol was added to the aqueous layer to extract the hydrazone. The octanol layer was recovered and the absorbance thereof was measured at 360 nm in a spectrophotometric microplate reader (Nippon Molecular Devices Co.; SPECTRAmax250).

(2) Preparation of Calibration Curve

Aqueous solutions of various glucose concentrations were prepared and the amounts of carbonyl compounds derived from glucose were assayed by the same method as described in (i); a calibration curve of glucose concentration vs. concentration of carbonyl compounds was prepared based on this experiment.

(3) Quantification of Carbonyl Compounds

Glucose concentrations in sample solutions were measured using a glucose assay kit (Wako Pure Chemical Industries, Ltd.; Glucose CII-Test Wako). The amount of carbonyl compounds derived from glucose was estimated by using the calibration curve. The amount of carbonyl compounds in the sample solution was determined by subtracting the amount of glucose-derived carbonyl compounds from the total amount of carbonyl compounds in the sample solution.

Figure 15:
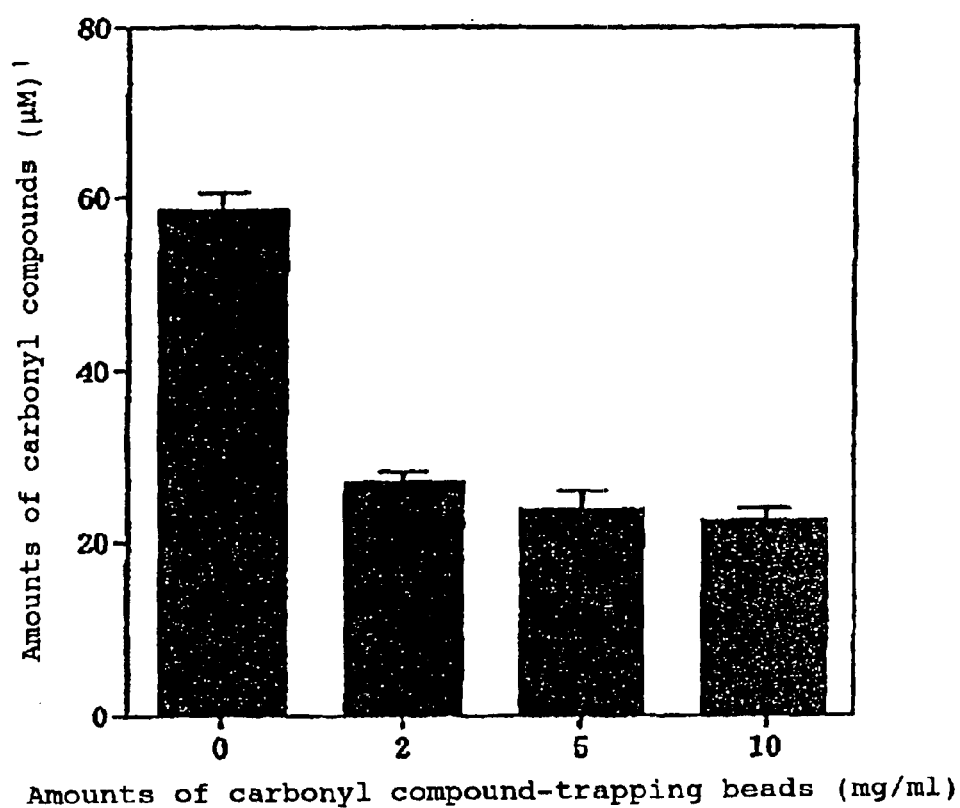
FIG. 15 shows the carbonyl compound-eliminating effect of carbonyl compound-trapping beads added to the peritoneal dialysate.

The results are shown in FIG. 15. The carbonyl compound-trapping beads (2 mg) were added to the peritoneal dialysate, and the suspension was stirred at room temperature for 16 hours. This treatment reduced the amount of carbonyl compounds by 55%. When 10 mg of carbonyl compound-trapping beads were added to the dialysate, the amount of carbonyl compounds was further reduced.

These findings clarified that the carrier with immobilized carbonyl compound-trapping agent can be used for inhibiting the generation and/or accumulation of carbonyl compounds in the peritoneal dialysate.

EXAMPLE 8
The Activity of Activated Charcoal in Trapping Carbonyl Compounds in a Dicarbonyl Compound Solution Activated charcoal was used as a carbonyl compound-trapping agent to evaluate its effect of eliminating carbonyl compounds from a dicarbonyl compound solution. A dicarbonyl compound solution was prepared by dissolving a dicarbonyl compound (100 μM) in a phosphate buffer (abbreviated hereafter "PBS"). The solution (900 μl) was added to a tube containing 25 μg or 50 μg of activated charcoal (Wako Pure Chemical Industries, Ltd.). Dicarbonyl compounds used were glyoxal, methylglyoxal, and 3-deoxyglucosone. The tube was placed on a rotator and stirred at room temperature for 19 hours. After stirring, the solution in the tube was filtered by a centrifugal filter tube (Millipore Co.; UFC30GV00) having membrane pores of 0.22 μm. The concentration of each dicarbonyl compound was determined by high performance liquid chromatography according to a commonly used method.

Figure 16:
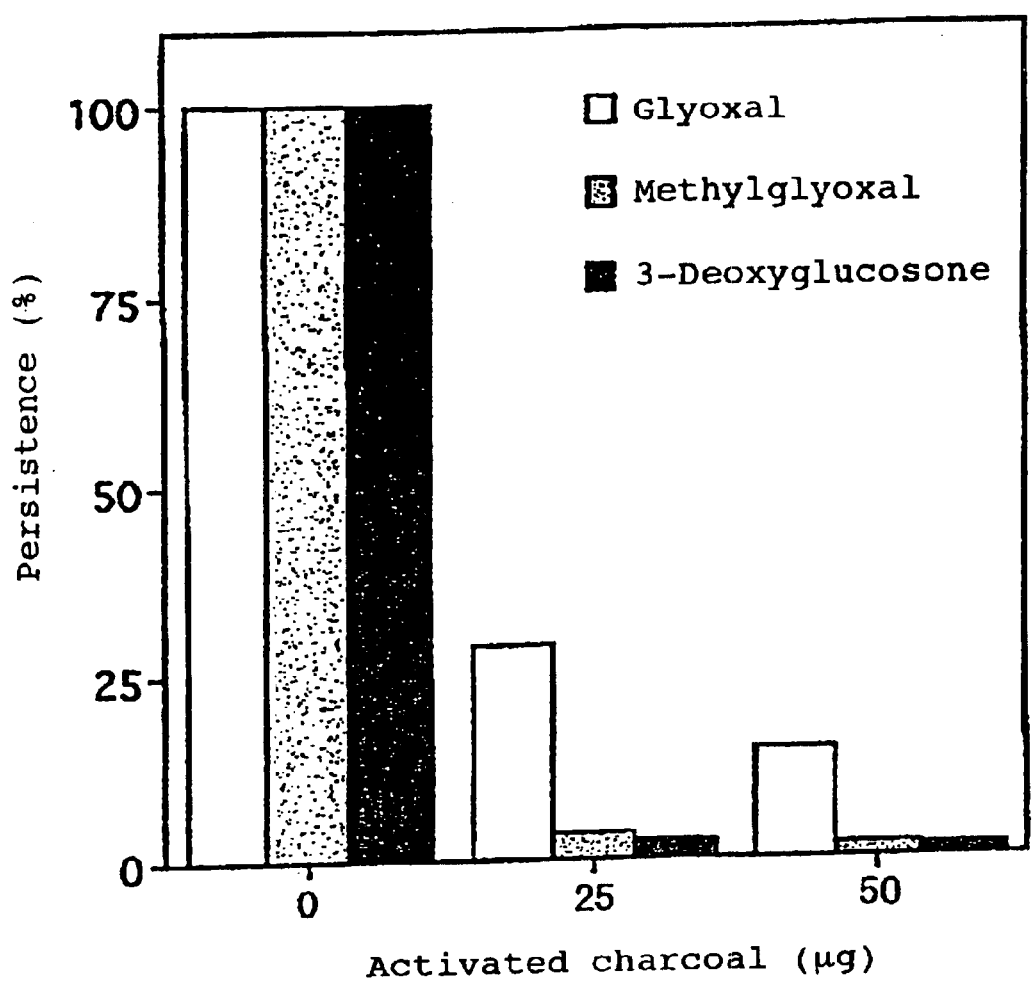
FIG. 16 shows the carbonyl compound-eliminating effect of activated charcoal added to a dicarbonyl compound solution.

The results are shown in FIG. 16. When 25 μg of activated charcoal was added to 900 μl of the dicarbonyl compound solution, the activated charcoal trapped glyoxal (GO) by 71%, methylglyoxal (MGO) by 94%, and 3-deoxyglucosone (3DG) by 93%. When 50 μg of activated charcoal was used, the charcoal trapped glyoxal by 85%, and both methylglyoxal and 3-deoxyglucosone by 98% Thus, it was confirmed that most of each dicarbonyl compound tested was trapped by activated charcoal.

EXAMPLE 9
The Activity of Activated Charcoal in Trapping Carbonyl Compound in the Peritoneal Dialysate Activated charcoal was used as a carbonyl compound-trapping agent to evaluate its effect of eliminating carbonyl compounds from the peritoneal dialysate. An aliquot (900 μl) of peritoneal dialysate (Baxter Ltd.; Dianeal PD-4, 1.5) was added to a tube containing 25 μg or 50 μg of activated charcoal (Wako Pure Chemical Industries, Ltd.). The tube was placed on a rotator and stirred at room temperature for 19 hours. After stirring, the solution in the tube was filtered by a centrifugal filter tube (Millipore Co.; UFC30GV00) having membrane pores of 0.22 μm. The concentrations of glyoxal, methylglyoxal, and 3-deoxyglucosone were determined by high performance liquid chromatography according to a commonly used method.

Figure 17:
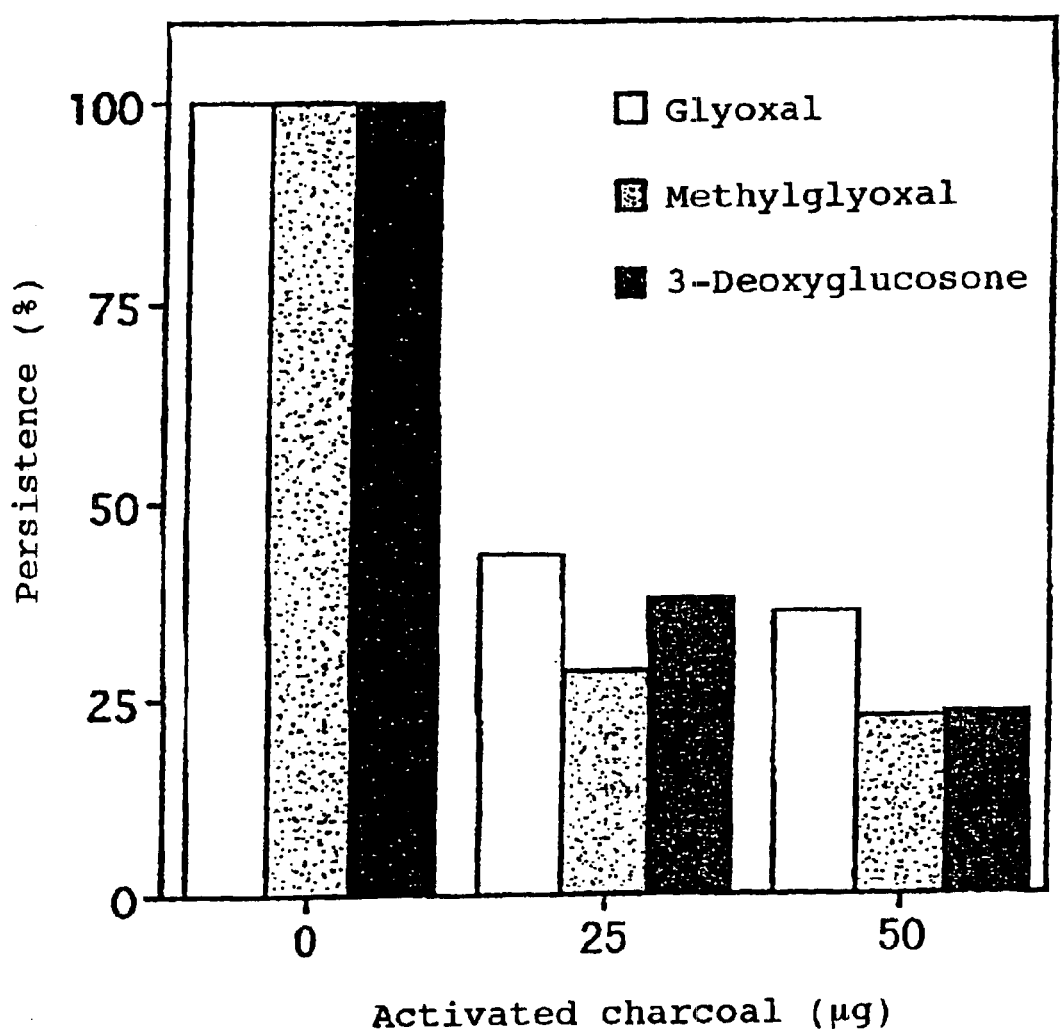
FIG. 17 shows the carbonyl compound-eliminating effect of activated charcoal added to the peritoneal dialysate.

The results are shown in FIG. 17. When 25 μg of activated charcoal was added to 900 μl of the peritoneal dialysate, the activated charcoal trapped glyoxal (GO) by 56%, methylglyoxal (MGO) by 71%, and 3-deoxyglucosone (3DG) by 62%, as compared with the dialysates without activated charcoal. When 50 μg of activated charcoal was used, the charcoal trapped glyoxal by 64%, methylglyoxal by 78%, and 3-deoxyglucosone by 77%. Thus, it was confirmed that each dicarbonyl compound tested was trapped by activated charcoal.

EXAMPLE 10
The Activities of Guanidine, Aminoguanidine, and Biguanide Agents in Trapping Glyoxal, Methylglyoxal, and 3-Deoxyglucosone A mixture (50 μl) of glyoxal, methylglyoxal, and 3-deoxyglucosone (1 mM each) was further mixed with 400 μl of 0.1 M phosphate buffer (pH 7.4), and each (50 μl; 30 mM) of guanidine, aminoguanidine, or a biguanide agent. The resulting mixture was incubated at 37° C. Biguanide agents used were metformin, buformin, and phenformin. After the incubation, glyoxal, methylglyoxal, and 3-deoxyglucosone were converted to quinoxaline derivatives by using o-phenylenediamine, and then the respective concentrations were determined by high performance liquid chromatography.

Figure 18:
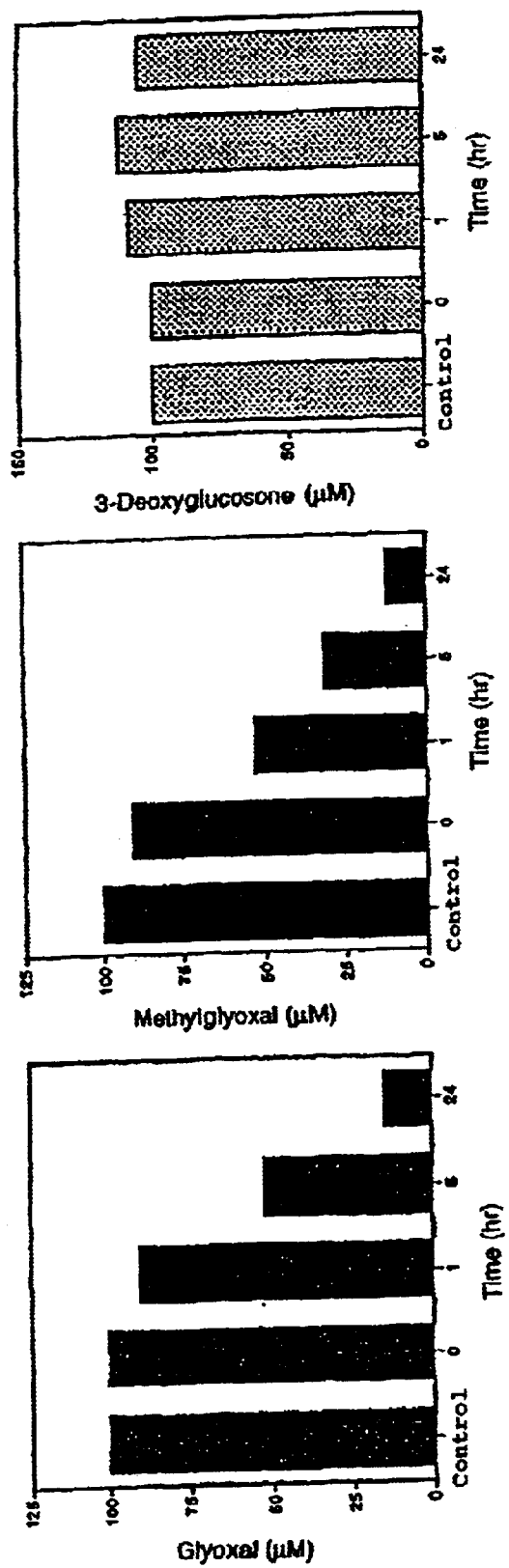
FIG. 18 shows the trapping activity of guanidine for glyoxal, methylglyoxal, and 3-deoxyglucosone.
Figure 19:
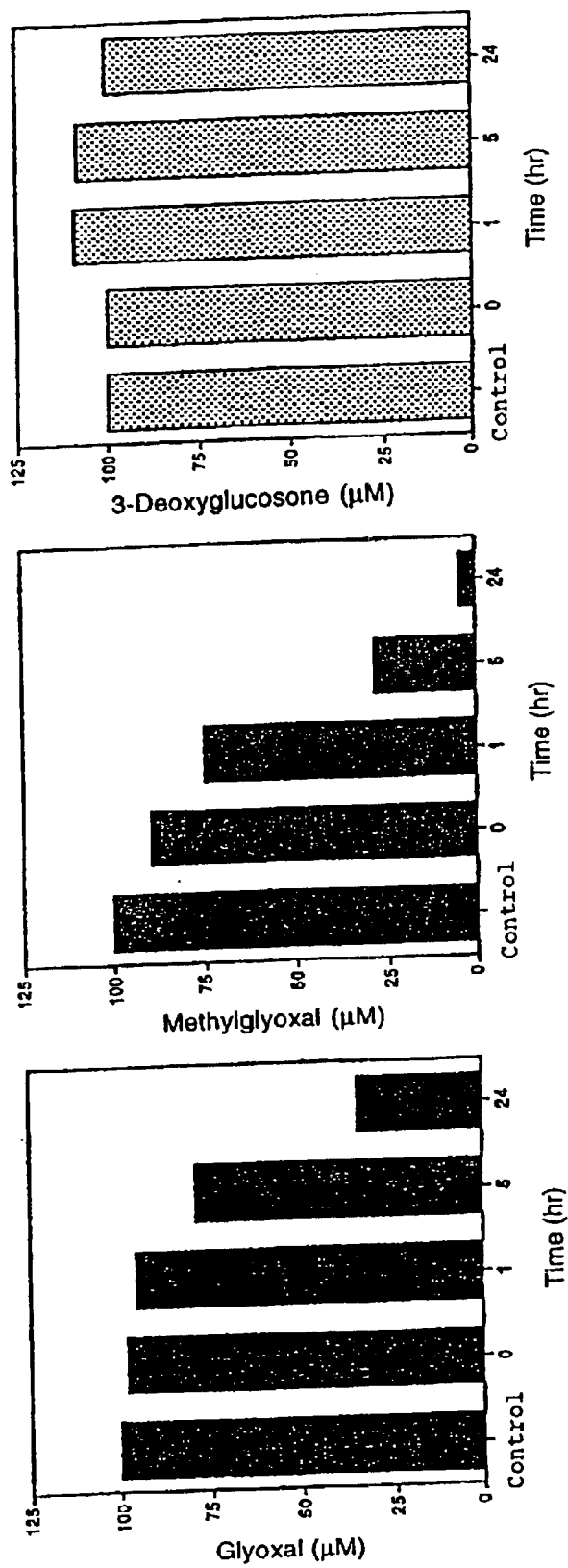
FIG. 19 shows the trapping activity of metformin, which is a biguanide, for glyoxal, methylglyoxal, and 3-deoxyglucosone.
Figure 20:
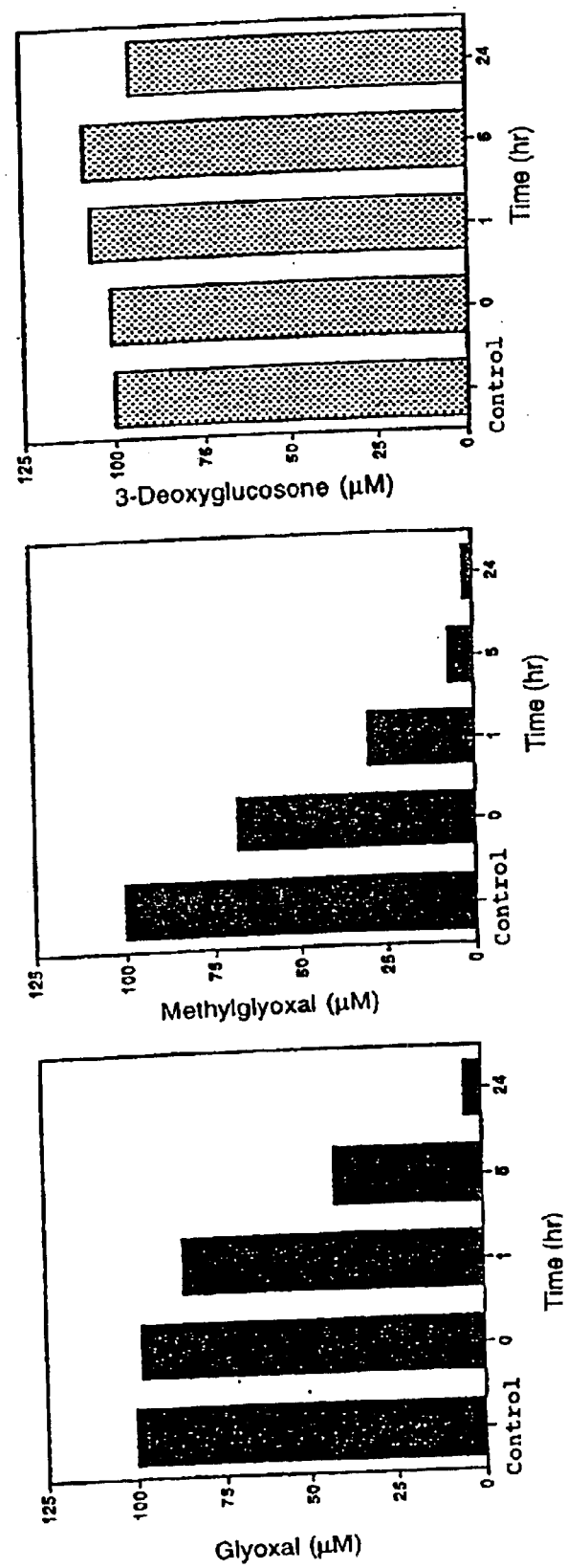
FIG. 20 shows the trapping activity of buformin, which is a biguanide, for glyoxal, methylglyoxal, and 3-deoxyglucosone.
Figure 21:
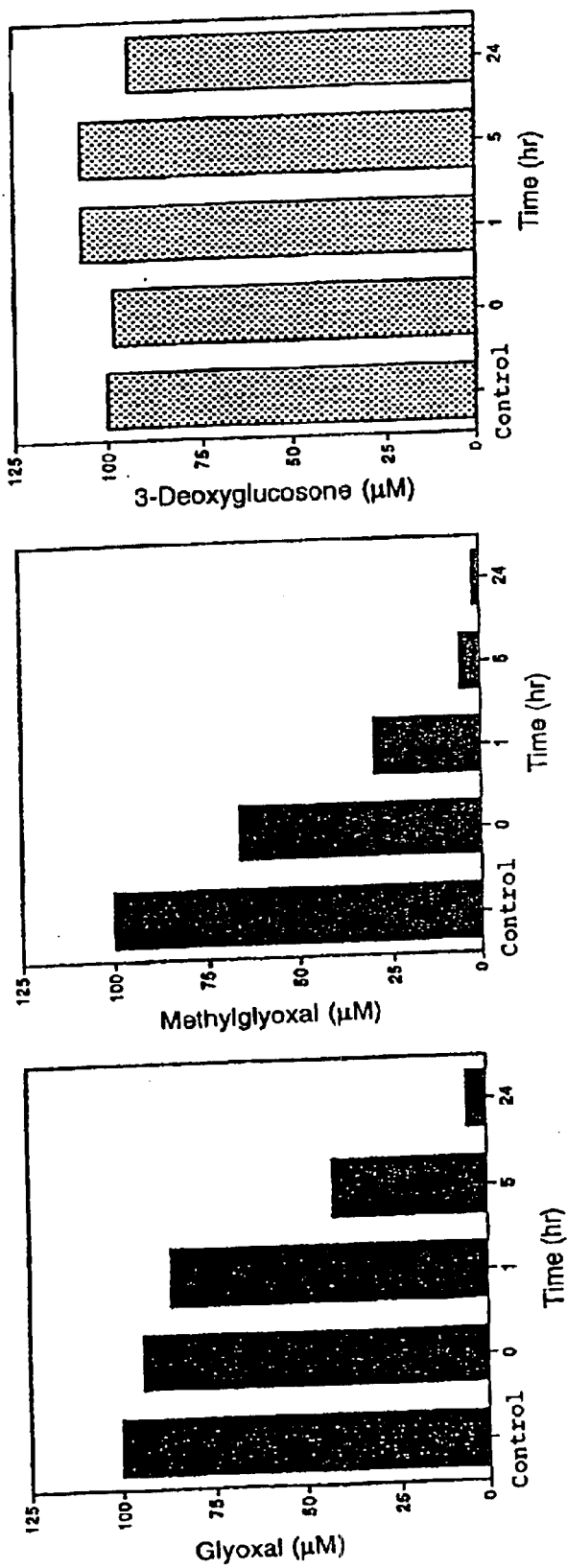
FIG. 21 shows the trapping activity of phenformin, which is a biguanide, for glyoxal, methylglyoxal, and 3-deoxyglucosone.
Figure 22:
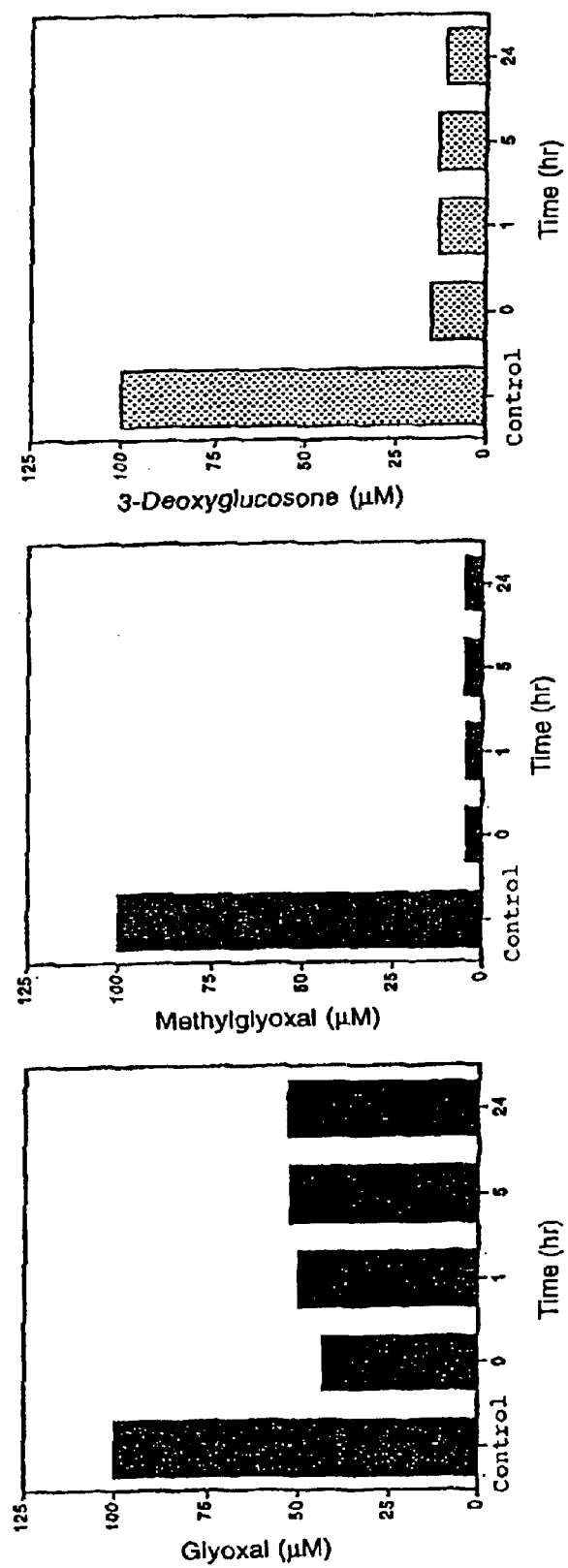
FIG. 22 shows the trapping activity of aminoguanidine for glyoxal, methylglyoxal, and 3-deoxyglucosone.

The results are shown in FIG. 18 (guanidine), FIG. 19 (metformin), FIG. 20 (buformin), FIG. 21 (phenformin), and FIG. 22 (aminoguanidine). Guanidine, aminoguanidine, and all the biguanide agents were shown to have the effect of markedly reducing the concentration of methylglyoxal, in particular. Further, aminoguanidine drastically reduced the concentration of methylglyoxal, and in addition, it has the effect of markedly reducing the concentration of 3-deoxyglucosone, which was not significantly reduced by other biguanides.

EXAMPLE 11
The Activity of SH Agent in Trapping Glyoxal, Methylglyoxal, and 3-Deoxyglucosone A solution (50 μl) of glyoxal, methylglyoxal, and 3-deoxyglucosone (1 mM each) was further mixed with 400 μl of 0.1 M phosphate buffer (pH 7.4) and an SH compound solution (50 μl; 30 mM). The resulting mixture was incubated at 37° C. SH compounds used were cysteine, N-acetylcysteine, and GSH. After the incubation, glyoxal, methylglyoxal, and 3-deoxyglucosone were converted to quinoxaline derivatives by using o-phenylenediamine, and then the respective concentrations were determined by high performance liquid chromatography.

Figure 23:
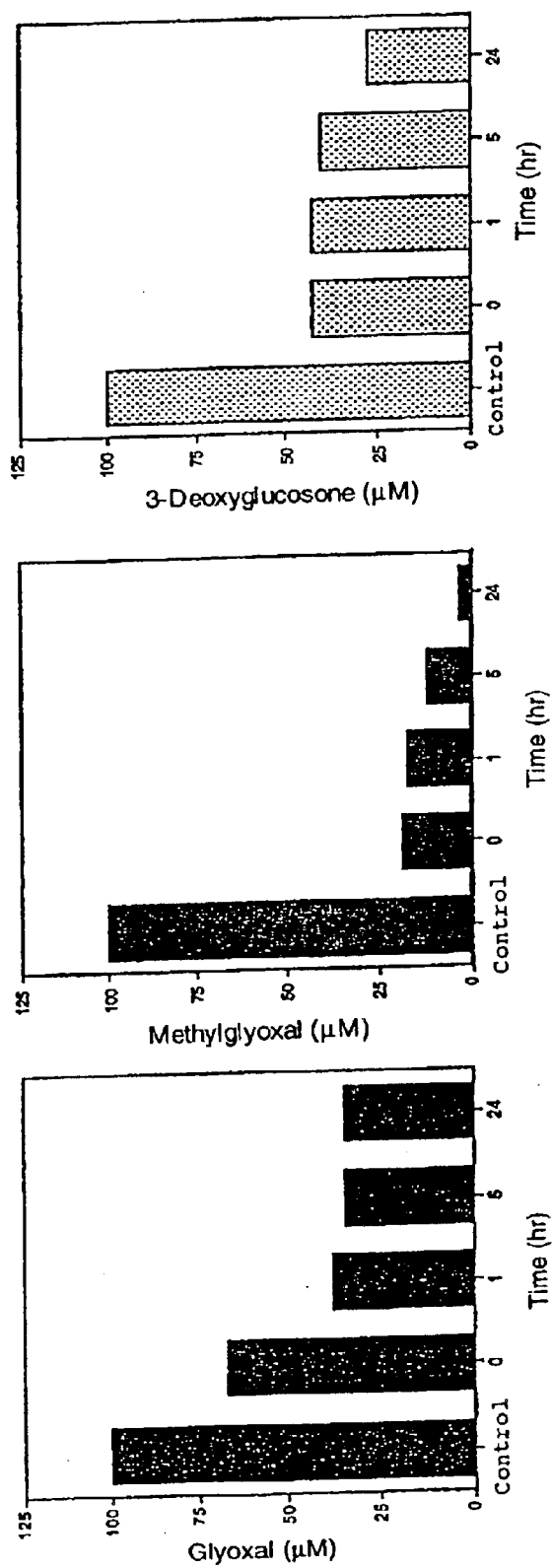
FIG. 23 shows the trapping activity of cysteine, which is an SH compound, for glyoxal, methylglyoxal, and 3-deoxyglucosone.
Figure 24:
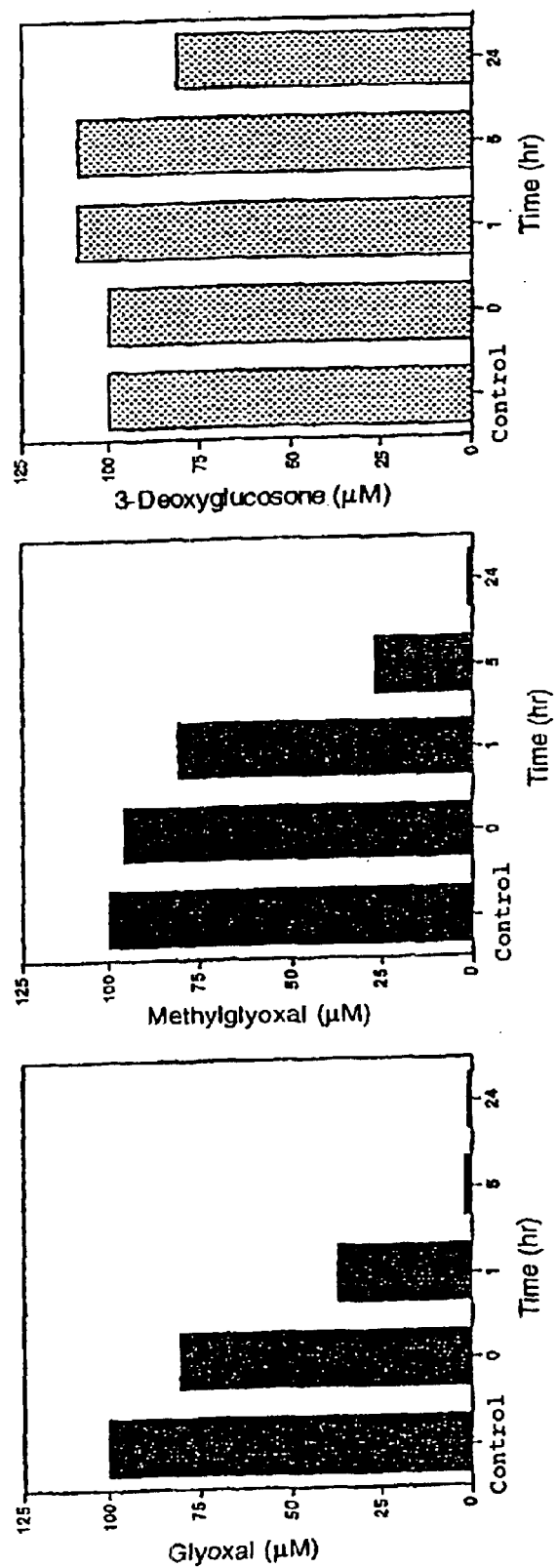
FIG. 24 shows the trapping activity of N-acetylcysteine, which is an SH compound, for glyoxal, methylglyoxal, and 3-deoxyglucosone.
Figure 25:
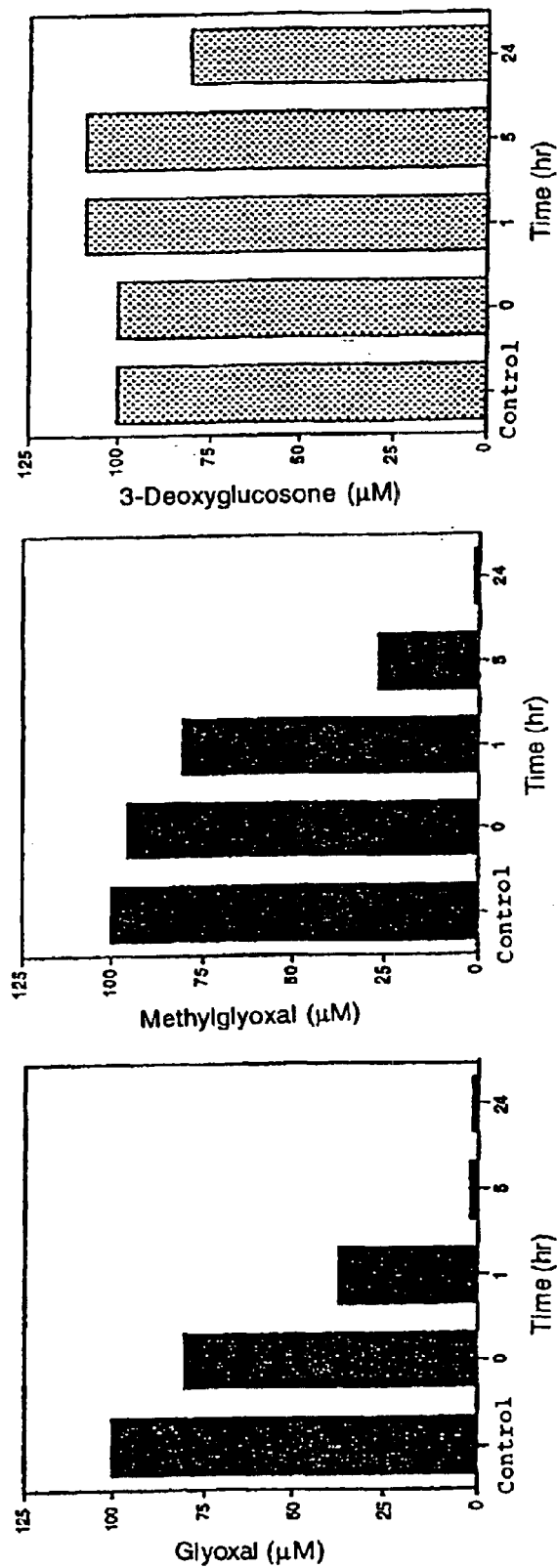
FIG. 25 shows the trapping activity of GSH, which is an SH compound, for glyoxal, methylglyoxal, and 3-deoxyglucosone.

The results are shown in FIG. 23 (cysteine), FIG. 24 (N-acetylcysteine), and FIG. 25 (GSH). All the SH compounds were found to have the effect of markedly reducing the concentrations of both glyoxal and methylglyoxal.

EXAMPLE 12
The Activity of Albumin in Trapping Glyoxal, Methylglyoxal, and 3-Deoxyglucosone A solution (50 µl) consisting of glyoxal, methylglyoxal, and 3-deoxyglucosone (1 mM each) was further mixed with 400 µl of 0.1 M phosphate buffer (pH 7.4), 50 µl of 100 mg/ml bovine serum albumin solution, and the resulting mixture was incubated at 37° C. After the incubation, glyoxal, methylglyoxal, and 3-deoxyglucosone were converted to quinoxaline derivatives by using o-phenylenediamine, and then the respective concentrations were determined by high performance liquid chromatography.

Figure 26:
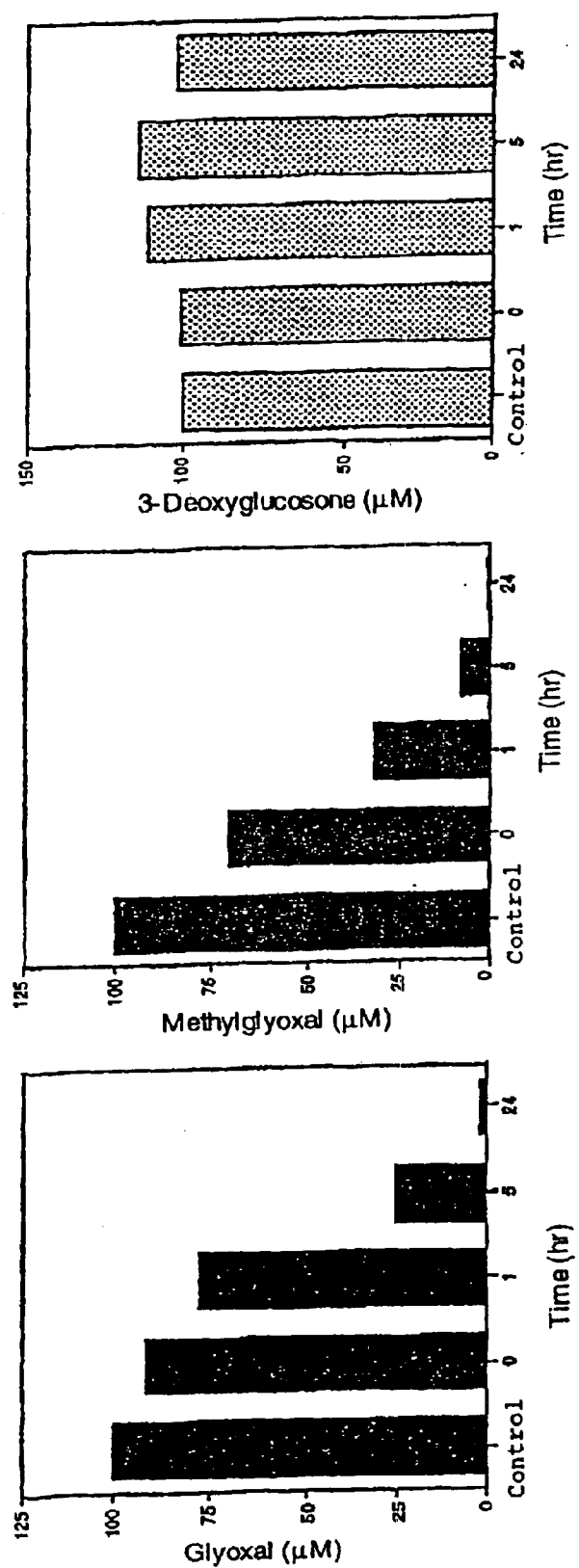
FIG. 26 shows the trapping activity of albumin, which is an SH compound, for glyoxal, methylglyoxal, and 3-deoxyglucosone.

The results are shown in FIG. 26. Bovine serum albumin was found to have the effect of markedly reducing the concentrations of glyoxal and methylglyoxal.

EXAMPLE 13
Effect of SH Compounds Added to the Peritoneal Dialysate and Incubated at 37° C on Inhibition of the Generation of Pentosidine An aliquot (490 µl) of a peritoneal dialysate (Baxter Ltd.; PD-4, 1.5) was mixed with 70 µl of 0.1 M phosphate buffer (pH 7.4) containing an SH compound and 140 µl of the peritoneal dialysate (Baxter Ltd.; PD-4, 1.5) containing 30 mg/ml bovine serum albumin. The resulting mixture was incubated at 37° C. for 1 week. SH compounds used were cysteine, N-acetylcysteine, and GSH. Aminoguanidine was also used. After the incubation, 50 µl of 10% trichloroacetic acid was added to the solution (50 µl). The mixture was centrifuged to precipitate the protein. The protein pellet was washed with 300 µl of 5% trichloroacetic acid, and then dried. Then, 100 µl of 6 N HCl was added to the protein pellet, and the dissolved protein was heated at 110° C. for 16 hours. The resulting sample was assayed for the quantification of pentosidine by high performance liquid chromatography (T. Miyata et al., 1996, J. Am. Soc. Nephrol., 7:1198–1206; T. Miyata et al., 1996, Proc. Natl. Acad. Sci. USA., 93:2353–2358).

Figure 27:
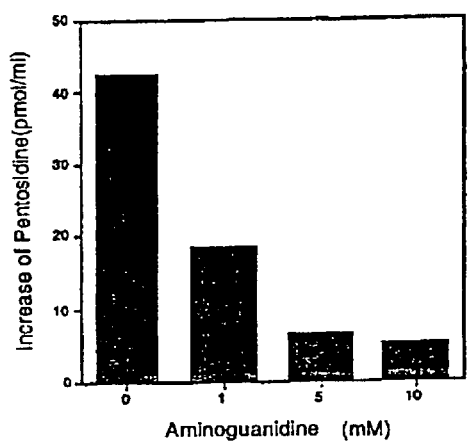
FIG. 27 shows the suppressing effect of SH compounds added to the peritoneal dialysate oh the generation of pentosidine.
Figure 27:
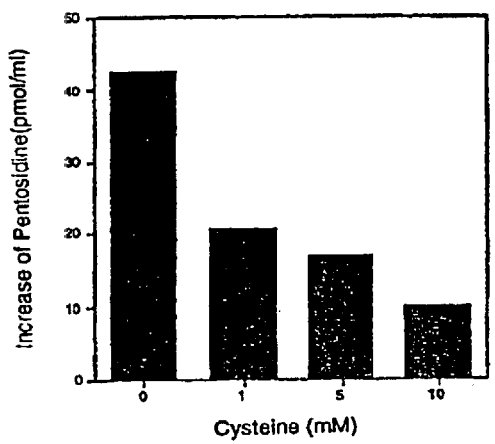
Figure 27:
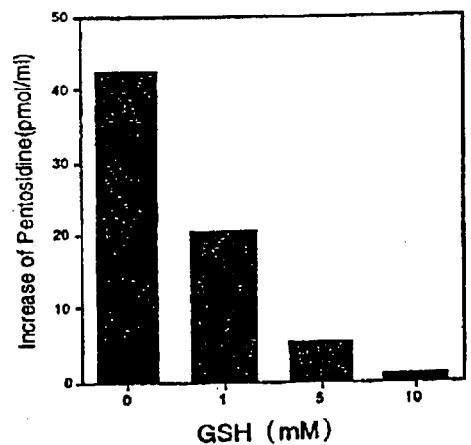
Figure 27:
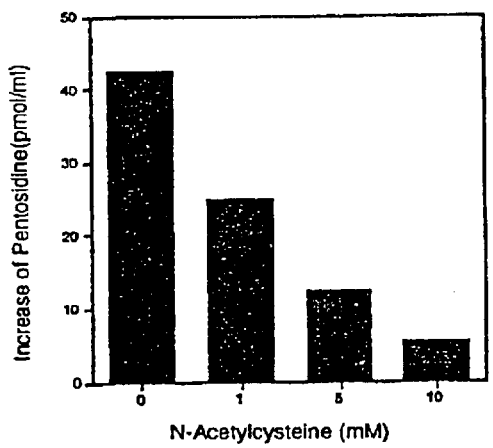

The results are shown in FIG. 27. It was revealed that the addition of SH compounds had a marked effect of inhibiting the generation of pentosidine.

INDUSTRIAL APPLICABILITY

The present invention can readily eliminate toxic damages caused by carbonyl compounds during peritoneal dialysis, which had been tormenting patients for a long time. When conventional peritoneal dialysates were used, the peritoneum of a patient being dialyzed was constantly under the carbonyl-stress state caused by carbonyl compounds, transferred to the peritoneal cavity from other parts of the body during dialysis, as well as by the carbonyl compounds generated in the process of manufacturing the dialysates. In contrast, the present invention can effectively eliminate carbonyl compounds generated in peritoneal dialysates, and therefore, can sufficiently contribute to the improvement of carbonyl stress of dialysis patients. Furthermore, carbonyl compounds transferred to the peritoneal cavity can also be inactivated or eliminated effectively by infusing a carbonyl compound-trapping agent or by circulating a dialysate through a carbonyl compound-trapping cartridge. Thus, the present invention provides a quite effective approach to prevent damages caused by peritoneal dialysis including peritoneal damages caused by carbonyl compounds associated with peritoneal dialysis.

In addition, the present invention enables removing carbonyl compounds generated by the degradation of glucose during heat sterilization and long-term storage, thereby successfully providing a peritoneal dialysate of neutral pH, which has previously been pharmaceutically difficult to prepare because of the degradation of glucose. Thus, the present invention enables a more physiological peritoneal dialysis treatment.

The inventive peritoneal dialysate can be practically used with only a simple procedure such as contacting with the carbonyl compound-trapping agent or administering directly. Furthermore, the production of inventive peritoneal dialysate does not require any specific facilities. Thus, the carbonyl compound-trapping agent based on the present invention, the peritoneal dialysate using the same, and the method of production thereof, creates a new therapeutic concept for peritoneal dialysis treatment.

---

What is claimed is:

1. A method for preparing a peritoneal dialysate having a reduced carbonyl compound content, the method comprising:

(a) contacting the peritoneal dialysate with a carbonyl compound-trapping agent; and (b) separating the peritoneal dialysate from the carbonyl compound-trapping agent.

2. A method for preparing a peritoneal dialysate having a reduced carbonyl compound content, comprising:

passing a peritoneal dialysate through an adsorbent cartridge comprising at least one carbonyl compound-trapping agent;

allowing the peritoneal dialysate to remain in contact with the adsorbent cartridge for a period of time and under conditions so as to allow carbonyl compounds present in the peritoneal dialysate to bind to the adsorbent cartridge; and recovering peritoneal dialysate having a reduced carbonyl compound content as compared to peritoneal dialysate entering the adsorbent cartridge.

3. The method of claim 2, wherein the carbonyl compound-trapping agent is comprised of aminoguanidine.

4. The method of claim 2, wherein the carbonyl compound-trapping agent is comprised of 2-isopropylidenehydrazono-4-oxo-thiazolidin-5-yl-acetanilide.

5. The method of claim 2, wherein the carbonyl compound-trapping agent comprises methylguanidine.

6. The method of claim 2, wherein the carbonyl compound-trapping agent comprises sulfonylhydrazine.

7. The method of claim 2, wherein the carbonyl compound-trapping agent is comprised of a compound chosen from pyrazolone, triazole, thiazoline, oxazole, pyridine, pyrimidine, benzothiazole, benzopyran, hydrazine, hydroquinone, benzoic acid, pyrrolonaphthyridinium, pyridoxamine, glutathione, cysteine, or N-acetylcysteine.

8. The method of claim 2, wherein the carbonyl compound-trapping agent comprises a composition chosen from activated charcoal, silica gel, alumina, and calcium carbonate.

9. The method of claim 2, wherein the carbonyl compound-trapping agent is chosen from activated charcoal, guanidine, aminoguanidine, biguanide, cysteine, and albumin.

* * * * *

UNITED STATES PATENT AND TRADEMARK OFFICE
CERTIFICATE OF CORRECTION

PATENT NO. : 6,919,326 B1
DATED : July 19, 2005
INVENTOR(S) : Miyata, Toshio et al.

It is certified that error appears in the above-identified patent and that said Letters Patent is hereby corrected as shown below:

Title page,
Item [73], Assignees, "Kurakawa" should be -- Kurokawa --;
Item [56], References Cited, FOREIGN PATENT DOCUMENTS, "EP 0 222 313 A2 5/1989" should be -- EP 0 222 313 A2 5/1987 --; and
OTHER PUBLICATIONS, "Lo et al.," reference, "...-32306" should be -- ...-32305 --.

Signed and Sealed this

Eighth Day of November, 2005

JON W. DUDAS
*Director of the United States Patent and Trademark Office*